(12) United States Patent
Quake et al.

(10) Patent No.: US 10,066,241 B2
(45) Date of Patent: *Sep. 4, 2018

(54) COMPOSITIONS AND METHODS OF DELIVERING TREATMENTS FOR LATENT VIRAL INFECTIONS

(71) Applicant: THE BOARD OF TRUSTEES OF THE LELAND STANFORD JUNIOR UNIVERSITY, Palo Alto, CA (US)

(72) Inventors: Stephen R. Quake, Palo Alto, CA (US); Jianbin Wang, Palo Alto, CA (US)

(73) Assignee: The Board of Trustees of The Leland Stanford Junior University, Stanford, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/725,943

(22) Filed: May 29, 2015

(65) Prior Publication Data
US 2015/0368670 A1    Dec. 24, 2015

Related U.S. Application Data

(60) Provisional application No. 62/029,072, filed on Jul. 25, 2014, provisional application No. 62/005,395, filed on May 30, 2014.

(51) Int. Cl.
| | | |
|---|---|---|
| *C12N 15/86* | (2006.01) | |
| *C12N 9/16* | (2006.01) | |
| *A61K 38/00* | (2006.01) | |
| *C12N 15/90* | (2006.01) | |
| *C12N 15/113* | (2010.01) | |
| *C12N 9/22* | (2006.01) | |

(52) U.S. Cl.
CPC ............ *C12N 15/907* (2013.01); *C12N 9/16* (2013.01); *C12N 9/22* (2013.01); *C12N 15/1133* (2013.01); *C12N 15/86* (2013.01); *A61K 38/00* (2013.01); *C12N 2310/20* (2017.05); *C12N 2330/51* (2013.01); *C12N 2810/60* (2013.01); *C12Y 301/00* (2013.01)

(58) Field of Classification Search
None
See application file for complete search history.

(56) References Cited

U.S. PATENT DOCUMENTS

| | | |
|---|---|---|
| 4,897,355 A | 1/1990 | Eppstein et al. |
| 4,946,787 A | 8/1990 | Eppstein et al. |
| 5,049,386 A | 9/1991 | Eppstein et al. |
| 5,208,036 A | 5/1993 | Eppstein et al. |
| 5,356,802 A | 10/1994 | Chandrasegaran |
| 5,436,150 A | 7/1995 | Chandrasegaran |
| 5,466,468 A | 11/1995 | Schneider et al. |
| 5,487,994 A | 1/1996 | Chandrasegaran |
| 5,580,571 A | 12/1996 | Hostetler |
| 5,626,869 A | 5/1997 | Nyqvist et al. |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,383,481 B1 | 5/2002 | Ikehara et al. |
| 6,410,248 B1 | 6/2002 | Greisman et al. |
| 6,453,242 B1 | 9/2002 | Eisenberg et al. |
| 6,534,261 B1 | 3/2003 | Cox, III et al. |
| 6,607,882 B1 | 8/2003 | Cox, III et al. |
| 6,890,554 B2 | 5/2005 | Jessee et al. |
| 7,166,298 B2 | 1/2007 | Jessee et al. |
| 8,697,359 B1 | 4/2014 | Zhang |
| 8,889,418 B2 | 11/2014 | Zhang et al. |
| 8,906,616 B2 | 12/2014 | Zhang et al. |
| 8,945,839 B2 | 2/2015 | Zhang |
| 8,993,233 B2 | 3/2015 | Zhang et al. |
| 9,487,802 B2 | 11/2016 | Quake et al. |
| 2005/0064474 A1 | 3/2005 | Urnov et al. |
| 2006/0188987 A1 | 8/2006 | Guschin et al. |
| 2006/0233770 A1* | 10/2006 | Ambinder .......... A61K 39/0011 424/93.21 |
| 2008/0131962 A1 | 6/2008 | Miller |
| 2009/0017543 A1 | 1/2009 | Wilkes et al. |
| 2010/0076057 A1 | 3/2010 | Sontheimer et al. |
| 2011/0023144 A1 | 1/2011 | Weinstein et al. |
| 2011/0177594 A1 | 7/2011 | Shushan et al. |
| 2012/0122213 A1 | 5/2012 | Lai et al. |
| 2013/0330778 A1 | 12/2013 | Zeiner et al. |
| 2014/0068797 A1 | 3/2014 | Doudna et al. |
| 2014/0186843 A1 | 7/2014 | Zhang et al. |
| 2014/0273037 A1 | 9/2014 | Wu |
| 2014/0273233 A1 | 9/2014 | Chen et al. |

(Continued)

FOREIGN PATENT DOCUMENTS

| | | |
|---|---|---|
| CN | 1584593 * | 2/2005 |
| CN | 103911376 A | 7/2014 |

(Continued)

OTHER PUBLICATIONS

Hsu et al., Development and Applications of CRISPR-Cas9 for Genome Engineering Cell 157, Jun. 5, 2014 pp. 1262-1278.*

(Continued)

*Primary Examiner* — Maria G Leavitt
(74) *Attorney, Agent, or Firm* — Kilpatrick Townsend and Stockton LLP

(57) ABSTRACT

The invention provides delivery methods and compositions for antiviral therapeutics. Methods and compositions are provided for targeted delivery of antiviral therapeutics into cells of interest using, for example, viral vectors such as adenovirus, AAV, and replication incompetent HSV. These and other delivery systems can be used as vehicles to deliver DNA vectors encoding a nuclease or a cell-killing gene. These delivery methods can also be used to deliver naked DNA or RNA, protein products, plasmids containing a promoter that is active only in a latent viral state which drives a cell-killing gene, or other therapeutic agents.

14 Claims, 20 Drawing Sheets

Specification includes a Sequence Listing.

(56) References Cited

U.S. PATENT DOCUMENTS

| | | |
|---|---|---|
| 2014/0295556 A1 | 10/2014 | Joung et al. |
| 2014/0315985 A1 | 10/2014 | May et al. |
| 2014/0342457 A1 | 11/2014 | Mali et al. |
| 2014/0342458 A1 | 11/2014 | Mali et al. |
| 2014/0349400 A1 | 11/2014 | Jakimo et al. |
| 2014/0356958 A1 | 12/2014 | Mali et al. |
| 2014/0357523 A1 | 12/2014 | Zeiner et al. |
| 2015/0024500 A1 | 1/2015 | Yu et al. |
| 2015/0045546 A1 | 2/2015 | Siksnys et al. |
| 2015/0050699 A1 | 2/2015 | Siksnys et al. |
| 2015/0056705 A1 | 2/2015 | Conway et al. |
| 2015/0232881 A1 | 8/2015 | Glucksmann et al. |
| 2015/0232883 A1 | 8/2015 | Dahlman et al. |
| 2015/0353905 A1 | 12/2015 | Weiss et al. |
| 2015/0376583 A1 | 12/2015 | Quake et al. |
| 2016/0060655 A1 | 3/2016 | Quake et al. |
| 2017/0049909 A1 | 2/2017 | Cullen et al. |
| 2017/0058299 A1 | 3/2017 | Horwitz et al. |
| 2017/0182190 A1 | 6/2017 | Quake et al. |

FOREIGN PATENT DOCUMENTS

| | | | |
|---|---|---|---|
| WO | 1991/016024 | | 10/1991 |
| WO | 1991/16024 | | 10/1991 |
| WO | 1991/17424 | | 11/1991 |
| WO | 19910/17424 | | 11/1991 |
| WO | 2001/037868 A1 | | 5/2001 |
| WO | WO 2004/027036 | * | 4/2004 |
| WO | 2005/028634 A2 | | 3/2005 |
| WO | 2005/084190 A2 | | 9/2005 |
| WO | 2007/097820 A2 | | 9/2005 |
| WO | 2007/071994 | | 6/2007 |
| WO | 2007/097820 A2 | | 8/2007 |
| WO | WO 2009/024834 | * | 2/2009 |
| WO | WO2011/119628 | * | 9/2011 |
| WO | 2013/141680 | | 9/2013 |
| WO | 2013/142578 | | 9/2013 |
| WO | 2013/176772 | | 11/2013 |
| WO | 2013/188037 | | 12/2013 |
| WO | 2014/071235 | | 5/2014 |
| WO | 2014/093479 | | 6/2014 |
| WO | 2014/093655 A2 | | 6/2014 |
| WO | 2014/099744 | | 6/2014 |
| WO | 2014/124226 | | 8/2014 |
| WO | 2014/143381 | | 9/2014 |
| WO | 2014/150624 | | 9/2014 |
| WO | 2014/165349 | | 10/2014 |
| WO | 2014/172470 | | 10/2014 |
| WO | 2015/006290 | | 1/2015 |
| WO | 2015/031775 | | 3/2015 |
| WO | 2015/034872 | | 3/2015 |
| WO | 2015/126927 A2 | | 8/2015 |
| WO | 2015/153889 A2 | | 10/2015 |
| WO | 2015/184259 | | 12/2015 |
| WO | 2015/184262 | | 12/2015 |
| WO | 2015/184268 | | 12/2015 |

OTHER PUBLICATIONS

Belfort, M. and Roberts, R., "Homing endonucleases: keeping the house in order," Nucleic Acids Res., 25(17):3379-3388, 1997.
Bernard, H., "Gene expression of genital human papillomaviruses and considerations on potential antiviral approaches," Antivir. Ther., 7:219-237, 2007.
Bhaya, D. et al., "CRISPR-Cas systems in bacteria and archaea: versatile small RNAs for adaptive defense and regulation," Annu. Rev. Genet., 45:273-297, 2011.
Bi, Y. et al., "High-efficiency targeted editing of large viral genomes by RNA-guided nucleases," PLOS Pathogens, 10(5):e1004090, 2014.
Bloom, K. et al., "Inactivation of hepatitis B virus replication in cultured cells and in vivo with engineered transcription activator-like effector nucleases," Molecular Therapy, 21(10):1889-1897, 2013.
Chang, N. et al., "Genome editing with RNA-guided Cas9 nuclease in zebrafish embryos," Cell Res 23:465-472, 2013.
Chen, J. et al., "Dynamic imaging of genomic loci in living human cells by an optimized CRISPR/Cas system," Cell, 155:1479-1491, 2013.
Chen, J. et al., "An efficient antiviral strategy for targeting hepatitis B virus genome using transcription activator-like effector nucleases," Molecular Therapy, 22(2): 303-311, 2013.
Cong, L. et al., "Multiplex genome engineering using CRISPR/Cas systems," Science, 339:819-823, 2013.
Ebina, H. et al., "Harnessing the CRISPR/Cas9 system to disrupt latent HIV-1 provirus," Scientific Reports, 3:2510/1-2510/2, 2013.
Gilbert, L. et al., "CRISPR—mediated modular RNA—guided regulation of transcription in eukaryotes," Cell, 154:442-451, 2013.
Glatzel, M. et al., "Adenoviral and adeno-associated viral transfer of genes to the peripheral nervous system," PNAS, 97(1):442-447, 2000.
Green, M. et al., "Epstein-Barr virus infection and posttransplant lymphoproliferative disorder," Am. J. Transplant., 13:41-54, 2013.
Harrison, M. et al., "A CRISPR view of development," Genes and Development, 28:1859-1872, 2014.
Horvath, P. and Barrangou, R. et al., "CRISPR/Cas, the immune system of bacteria and archaea," Science, 327:167-170, 2010.
Hoshino, Y. et al., "The number of herpes simplex virus-infected neurons and the number of viral genome copies per neuron correlate with latent viral load in ganglia," Virology, 372(1):56-63, 2008.
Hsu, P. et al., "Development and applications of CRISPR-Cas9 for genome engineering," Cell, 157:1262, 2014.
Hsu, P. et al., "DNA targeting specificity of RNA—guided Cas9 nucleases," Nature Biotechnology, 31(9):827-832, 2013.
Hu, W. et al., "RNA—directed gene editing specifically eradicates latent and prevents new HIV-1 infection," PNAS, 111(31):11461-6, 2014.
Hwang, W. et al., "Efficient genome editing in zebrafish using a CRISPR-Cas system," Nat. Biotechnol., 31:227-229, 2013.
Jinek, M. et al., "RNA—programmed genome editing in human cells," eLife 2:e00471, 2013.
Jinek, M. et al., "A programmable dual-RNA—guided DNA endonuclease in adaptive bacterial immunity," Science, 337:816-821, 2012.
Joung, J. and Sander, J., "TALENs: a widely applicable technology for targeted genome editing," Nat Rev Mol Cell Bio, 14:49-55, 2013.
Lee, H. et al., "Enhancing transfection efficiency using polyethylene glycol grafted polyethylenimine and fusogenic peptide," Biotechnol. Bioprocess Eng, 6:269-273, 2001.
Liu, B. et al., "CMV enhancer/human PDGF—beta promoter for neuron specific transgene expression," Gene Ther., 11(1):52-60, 2004.
Mali, P. et al, "RNA—guided human genome engineering via Cas9," Science, 339:823-826, 2013.
Mali, P. et al., "Cas9 as a versatile tool for engineering biology," Nat Meth 10(10):957, 2013.
Münger, K. et al., "Mechanisms of human papillomavirus—induced oncogenesis," J. Virol., 78(21):11451-11460, 2004.
Naito, Y. et al., "CRISPRdirect: software for designing CRISPR/Cas guide RNA with reduced off-target sites," Bioinformatics, 3 pages, 2014, retrieved online at <http://bioinformatics.oxfordjournals.org/ on Apr. 28, 2015.
Nishimasu, H. et al., "Crystal structure of Cas9 in complex with guide RNA and target DNA," Cell 156:935-949, 2014.
Qi, L. et al., "Repurposing CRISP as an RNA—guided platform for sequence—specific control of gene expression," Cell, 152:1173-1183, 2013.
Qu, X. et al., "Zinc-finger-nucleases mediate specific and efficient excision of HIV-1 proviral DAN from infected and latently infected human T cells," Nucl Ac Res 41(16):7771-7782, 2013.
Ran, F. et al., "Double nicking by RNA-guided CRISPR/Cas9 for enhanced genome editing specificity," Cell, 154(6):1380-1389, 2013.

(56) References Cited

OTHER PUBLICATIONS

Ruf, I. et al., "Epstein-Barr virus regulates c-MYC, apoptosis, and tumorigenicity in burkitt lymphoma," Molecular and Cellular Biology 19:1651-1660, 1999.
Schiffer, J. et al., "Targeted DNA mutagenesis for the cure of chronic viral infections," J. Virol., 88(17):8920-8936, 2012.
Schiffer, J.T. et al., "Predictors of hepatitis B cure using gene therapy to deliver DNA cleavage enzymes: a mathematical modeling approach," PLoS Comput. Biol., 9(7): e1003131, 2013.
Schwank, G. et al., "Functional repair of CFTR by CRISPR/Cas9 in intestinal stem cell organoids of cystic fibrosis patients," Cell Stem Cell, 13(6):653-8, 2013.
Silva, G. et al., "Meganucleases and other tools for targeted genome engineering," Curr Gene Ther, 11(1):11-27, 2011.
Sternberg et al., "DNA interrogation by the CRISPR RNA—guided endonuclease Cas9," Nature, 507(7490):62-67 , 2014.
Terns, M. and Terns, R., "CRISPR—based adaptive immune systems," Curr Op Microb, 14:321-327, 2011.
Wah, D. et al., "Structure of FokI has implications for DNA cleavage," PNAS 95:10564-10569, 1998.
Wang, J. and Quake, S., "RNA—guided endonuclease provides a therapeutic strategy to cure latent herpesviridae infection," PNAS, 111(36):13157-13162, 2014.
Wang, H. et al., "One-step generation of mice carrying mutations in multiple genes by CRISPR/Cas-mediated genome engineering," Cell, 153:910-918, 2013.
Westergaard, M. et al., "Modulation of keratinocyte gene expression and differentiation by PPAR—selective ligands and tetradecyltheioacetic acid," J. Invest. Dermatol., 116(5):702-12, 2001.
Wiedenheft, B. et al., "RNA—guided genetic silencing systems in bacteria and archaea," Nature, 482:331-338, 2012.
Wikipedia, "Transcription activator—like effector nuclease," 7 pages, retrieved online at <https://en.wikipedia.org/wiki/Transcription_activator-like_effector_nuclease> on Feb 25, 2016.
Xiao, A. et al., "Chromosomal deletions and inversions mediated by TALENS and CRISPR/Cas in zebrafish," Nucl. Acids Res., 1-11, 2013.
Xue, Z. et al., "Efficient gene knock-out and knock-in with transgenic Cas9 in *Drosophila*," G3 Genes Genomes genetics, 4:925-929, 2014.
Yang, H. et al., "One-step generation of mice carrying reporter and conditional alleles by CRISPR/Cas—mediated genome engineering," Cell, 154:1370-1379, 2013.
Zheng, Z. and Baker, C., "Papillomavirus genome structure, expression, and post-transcriptional regulation," Front Biosci, 11:2286-2302, 2006.
Belfort & Roberts, 1997, Homing endonucleases: keeping the house in order, Nucleic Acids Res 25(17):3379-3388.
Bernard, 2007, Gene expression of genital human papillomaviruses and considerations on potential antiviral approaches. Antivir.Ther. 7:219-237.
Bhava et al., 2011, CRISPR-Cas systems in bacteria and archea: versitle small RNAs for adaptive defense and regulation, Annu Rev Genet 45:273-297.
Bi, Yanwei et al., "High-Efficiency Targeted Editing of Large Viral Genomes by RNA—Guided Nucleases," PLOS Pathogens, vol. 10, No. 5, May 2014, p. e1004090.
Chang et al., 2013, Genome editing with RNA—guided Cas9 nuclease in zebrafish embryos, Cell Res 23:465-472.
Chen et al., 2013, Dynamic Imaging of Genomic Loci in Living Human Cells by an Optimized CRISPR/Cas System. Cell 155:1479-1491.
Chen, Jieliang et al., "An Efficient Antiviral Strategy for Targeting Hepatitis B Vvirus Genome Using Transcription Activator-Like Effector Nucleases," Molecular Therapy, vol. 22, No. 2, Sep. 12, 2013, pp. 303-311.
Cong et al., 2013, Multiplex Genome Engineering Using CRISPR/Cas Systems, Science 339:819-823.

Ebina, Hirotaka et al., "Harnessing the CRISPR/Cas9 system to disrupt latent HIV-1 provirus," Scientific Reports, vol. 3, Aug. 26, 2013, pp. 2510/1-2510/2.
Gilbert et al., 2013, CRISPR—mediated modular RNA—guided regulation of transcription in eukaryotes, Cell 154:442-451.
Glatzel et al., 2000, Adenoviral and adeno-associated viral transfer of genes to the peripheral nervous system PNAS 97(1):442-447.
Harrison et al., 2014, A CRISPR view of development, Genes and Development 28:1859-1872.
Horvath et al., 2010, CRISPR/Cas, the immune system of bacteria and archaea, Science 327:167-170.
Hoshino et al., 2008, The number of herpes simplex virus-infected neurons and the number of viral genome copies per neuron correlate with latent viral load in ganglia, Virology 372(1):56-63.
Hsu et al., 2014, Development and applications of CRISPR-Cas9 for genome engineering, Cell 157:1262.
Hsu, 2013, DNA targeting specificity of RNA—guided Cas9 nucleases, Nature Biotechnology 31(9):827-832.
Hu et al., 2014, RNA—directed gene editing specifically eradicates latent and prevents new HIV-1 infection, PNAS 111(31):11461-6.
Hwang et al., 2013, Efficient genome editing in zebrafish using a CRISPR-Cas system, Nat. Biotechnol 31:227-229.
Jinek et al., 2013, RNA—programmed genome editing in human cells, eLife 2:e00471.
Jinek, 2012, A programmable dual-RNA—guided DNA endonuclease in adaptive bacterial immunity, Science 337:816-821.
Joung & Sander, 2013, TALENs: a widely applicable technology for targeted genome editing, Nat Rev Mol Cell Bio 14:49-55.
Liu et al., 2004, CMV enhancer/human PDGF—beta promoter for neuron specific transgene expression, Gene Ther 11(1):52-60.
Mali et al, 2013, RNA—guided human genome engineering via Cas9, Science 339:823-826.
Mali et al., 2013, Cas9 as a versatile tool for engineering biology, Nat Meth 10(10):957.
Munger et al., 2004, Mechanisms of human papillomavirus-induced oncogenesis, J Virol 78(21):11451-11460.
Naito et al., 2014, CRISPRdirect: software for designing CRISPR/Cas guide RNA with reduced off-target sites, Bioinformatics.
Nishimasu et al., 2014, Crystal structure of Cas9 in complex with guide RNA and target DNA, Cell 156:935-949.
Qi et al., 2013, Repurposing CRISP as an RNA—guided platform for sequence—specific control of gene expression, Cell 152:1173-1183.
Qu et al., 2013, Zinc-finger-nucleases mediate specific and efficient excision of HIV-1 proviral DAN from infected and latently infected human T cells, Nucl Ac Res 41(16):7771-7782.
Ran, F. Ann et al., "Double Nicking by RNA—guided CRISPR/Cas9 for Enhanced Genome Editing Specificity," Cell, vol. 154, No. 6, Sep. 12, 2013, pp. 1380-1389.
Ruf et al., 1999, Epstein-Barr Virus Regulates c-MYC, Apoptosis, and Tumorigenicity in Burkitt Lymphoma, Molecular and Cellular Biology 19:1651-1660.
Schiffer, 2012, Targeted DNA mutagenesis for the cure of chronic viral infections, J Virol 88(17):8920-8936.
Schwank et al., 2013, Functional repair of CFTR by CRISPR/Cas9 in intestinal stem cell organoids of cystic fibrosis patients, Cell Stem Cell 13(6):653-8.
Silva et al., 2011, Meganucleases and other tools for targeted genome engineering, Curr Gene Ther 11(1):11-27.
Sternberg et al., 2014, DNA interrogation by the CRISPR RNA—guided endonuclease Cas9, Nature 507(7490):62-67.
Terns et al., 2011, CRISPR—based adaptive immune systems, Curr Op Microb 14:321-327.
Wah et al., 1998, Structure of FokI has implications for DNA cleavage, PNAS 95:10564-10569.
Wang & Quake, 2014, RNA—guided endonuclease provides a therapeutic strategy to cure latent herpesviridae infection, PNAS 111(36):13157-13162.
Wang et al., 2013, One-step generation of mice carrying mutations in multiple genes by CRISPR/Cas—mediated genome engineering, Cell 153:910-918.

(56) References Cited

OTHER PUBLICATIONS

Westergaard et al., 2001, Modulation of keratinocyte gene expression and differentiation by PPAR-selective ligands and tetradecyltheioacetic acid, J Invest Dermatol 116(5):702-12.

Wiedenheft et al., 2012, RNA—guided genetic silencing systems in bacteria and archaea, Nature 482:331-338.

Xiao et al., 2013, Chromosomal deletions and inversions mediated by TALENS and CRISPR/Cas in zebrafish, Nucl Acids Res 1-11.

Xue et al., 2014, Efficient gene knock-out and knock-in with transgenic Cas9 in *Drosophila*, G3 4:925-929.

Yang et al., 2013, One-step generation of mice carrying reporter and conditional alleles by CRISPR/Cas—mediated genome enginneering, Cell 154:1370-1379.

Zheng & Baker, 2006, Papillomavirus genome structure, expression, and post-transcriptional regulation, Front Biosci 11:2286-2302.

Jaffrey, S., "An expanding universe of mRNA modifications," Nature Structural & Molecular Biology, 21(11):945-946, 2014.

Hui, S. et al., "High-efficiency loading, transfection, and fusion of cells by electroporation in two-phase polymer systems," Biophysical Journal, 71:1123-30, 1996.

Peng, R. et al., "Sequence and functional analysis of EBNA-LP and EBNA2 proteins from nonhuman primate lymphocryptoviruses," J. Virology, 74(1):379-389, 2000.

Longo, P. et al., "Transient mammalian cell transfection with Polyethylenimine (PEI)," Methods in Enzymology, 529:227-240, 2013.

Xu, J. et al., "Enhancement of mucosal and cellular immune response in mice by vaccination with respiratory syncytial virus DNA encapsulated with transfersome," Viral Immunol., 21(4):483-9, 2008.

Zhen, S. et al., "In vitro and in vivo growth suppression of human papillomavirus 16-positive cervical cancer cells by CRISPR/Cas9," Biochemical and Biophysical Research Communications, 450(4):1422-6, 2014.

\* cited by examiner

SEQUENCE LISTING

```
<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Synthetic sgEBV1 guide RNA targeting Sequence

<400> SEQUENCE: 1
gccctggacc aacccggccc                                                     20

<210> SEQ ID NO 2
<211> LENGTH: 20
<212> TYPE: DNA
<213> ORGANISM: Artificial Sequence
<220> FEATURE:
<223> OTHER INFORMATION: Synthetic sgEBV2 guide RNA targeting Sequence

<400> SEQUENCE: 2
ggccgctgcc ccgctccggg                                                     20

<210> SEQ ID NO 3
<211> LENGTH: 19
<212> TYPE: DNA
<213> ORGANISM: Artificial Sequence
<220> FEATURE:
<223> OTHER INFORMATION: Synthetic sgEBV3 guide RNA targeting Sequence

<400> SEQUENCE: 3
ggaagacaat gtgccgcca                                                      19

<210> SEQ ID NO 4
<211> LENGTH: 20
<212> TYPE: DNA
<213> ORGANISM: Artificial Sequence
```

```
<220> FEATURE:
<223> OTHER INFORMATION: Synthetic sgEBV4 guide RNA targeting Sequence

<400> SEQUENCE: 4
tctggaccag aaggctccgg                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic sgEBV5 guide RNA targeting Sequence

<400> SEQUENCE: 5
gctgccgcgg agggtgatga                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic sgEBV6 guide RNA targeting Sequence

<400> SEQUENCE: 6
ggtggcccac cgggtccgct                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic sgEBV7 guide RNA targeting Sequence

<400> SEQUENCE: 7
gtcctcgagg gggccgtcgc                                               20
```

COMPOSITIONS AND METHODS OF DELIVERING TREATMENTS FOR LATENT VIRAL INFECTIONS

CROSS-REFERENCE TO RELATED APPLICATION(S)

This application claims priority to, and the benefit of, both U.S. Provisional Patent Application Ser. No. 62/005,395, filed May 30, 2014, and U.S. Provisional Patent Application Ser. No. 62/029,072, filed Jul. 25, 2014, the contents of which are incorporated by reference.

STATEMENT AS TO RIGHTS TO INVENTIONS MADE UNDER FEDERALLY SPONSORED RESEARCH AND DEVELOPMENT

This invention was made with Government support under contracts CA139490, CA151459, HL099995, and HL099999 awarded by the National Institutes of Health. The Government has certain rights in the invention.

REFERENCE TO A SEQUENCE LISTING

The Sequence Listing written in file SequenceListing_79445-946248.txt, created on Sep. 8, 2015, 1,946 bytes, machine format IBM-PC, MS-Windows operating system, is hereby incorporated by reference in its entirety for all purposes.

FIELD OF THE INVENTION

The invention relates to delivering therapeutics to virus-infected cells.

BACKGROUND

Viral infections are a significant medical problem. For example, herpes is a widespread human pathogen, with more than 90% of adults having been infected. Due to latency, once infected, a host carries the herpes virus indefinitely, even when not expressing symptoms. Similarly, human papillomavirus, or HPV is a common virus in the human population, where more than 75% of people will be infected. A particular problem is that viral infections may lead to cancer. For example, integration of HPV into host DNA is known to result in cancer, specifically cervical cancer. The Epstein-Barr virus (EBV) not only causes infectious mononucleosis (glandular fever), but is also associated with cancers such as Hodgkin's lymphoma and Burkitt's lymphoma.

Efforts are made to develop drugs that target viral proteins but those efforts have not been wholly successful. For example, where a virus is in a latent state, not actively expressing its proteins, there is nothing to target. Additionally, any effort to eradicate a viral infection is not useful if it interferes with host cellular function. For example, an enzyme that prevents viral replication is not helpful if it interferes with genome replication in cells throughout the host.

SUMMARY

The invention provides methods and therapeutics for selectively treating a viral infection in host cells that are infected by the virus. The treatment can include causing the death of host cells but only those cells that are infected. For example, the treatment can include delivering a gene for a protein that causes cell death, where the gene is under control of a viral regulatory element such as a promoter from the genome of the infecting virus or the gene is encoded in a vector that includes a viral origin of replication. Where the virus is present, the gene will be expressed and the gene product will cause the death of the cell. The gene can code for a protein important in apoptosis, or the gene can code for a nuclease that digests the host genome.

Alternatively, the treatment can include an antiviral therapeutic that removes the viral infection without interfering with host cell function. For example, the treatment may include a targetable nuclease that is targeted to viral nucleic acid. The targetable nuclease can be provided in a gene that is under the control of a viral regulatory element such as a viral promoter or an origin of replication. The invention provides for targeted delivery of antiviral therapeutics into cells of interest using, for example, viral vectors such as adenovirus, AAV, and replication incompetent HSV. These and other delivery systems can be used as vehicles to deliver nucleic acid (DNA, RNA, synthetic nucleic acids, such as PNA, LNA, etc) vectors encoding a nuclease or a cytotoxic genetic cassette. Delivery methods of the invention are useful to deliver vectors containing antiviral gene editing sequences. The invention also contemplates delivering naked DNA or RNA, protein products, plasmids containing a promoter or other regulatory sequence that is active only in a latent viral state which controls a cell-killing genetic construct, or expression of a therapeutic agent (e.g., a cytotoxic protein).

In certain aspects, the invention provides a composition for treating a viral infection. The composition includes a vector that includes a gene for a therapeutic and a sequence that causes the therapeutic to be expressed within a cell that is infected by a virus. The sequence may be a regulatory element (e.g., a promoter and an origin of replication) from the genome of the virus.

The therapeutic may provide a mechanism that selectively causes death of virus-infected cells. In certain embodiments, the therapeutic comprises a protein that causes death of virus-infected cells. The therapeutic may be a protein that selectively causes the death of the virus-infected cells. For example, a protein may be used that restores a deficient apoptotic pathway in the cell. The gene may be, for example, BAX, BAK, BCL-2, or alpha-hemolysin. Preferably, the therapeutic induces apoptosis in the cell that is infected by the virus and does not induce apoptosis in an uninfected cell.

In some embodiments, the therapeutic is a targetable nuclease and the sequence is from a genome of the virus. For example, the targetable nuclease may be cas9 endonuclease and the vector may further encode a plurality of guide RNAs. The guide RNAs may be designed to target the genome of the cell that is infected by the virus.

In certain embodiments, the promoter only causes the therapeutic to be expressed within a cell that is in a state of latent infection by the virus.

The vector may be a viral vector such as, for example, a retrovirus, lentivirus, adenovirus, herpesvirus, poxvirus, alphavirus, vaccinia virus, or adeno-associated viruses. The vector may include a plasmid. The vector may include a nanoparticle, cationic lipids, a cationic polymers, a metallic nanoparticle, a nanorod, a liposome, a micelle, a microbubble, a cell-penetrating peptide, or a liposphere.

In some aspects, the invention provides a composition for treating a viral infection. The composition includes a vector that includes an antiviral therapeutic and a regulatory element that causes the therapeutic to be active within a cell that is infected by a virus. The antiviral therapeutic may optionally be a gene for a targetable nuclease (e.g., cas9, ZFN, TALENS, a meganuclease) and the regulatory element may be from a genome of the virus (e.g., a promoter or an origin of replication). The vector may encode a guide RNA that targets the nuclease to nucleic acid from a genome of the virus. In certain embodiments, the guide RNA is designed to have no perfect match in a human genome. The guide RNAs may target the nuclease to a regulatory element in the genome of the virus. Any suitable virus may be treated such as Adenovirus, Herpes simplex, type 1, Herpes simplex, type 2, Varicella-zoster virus, Epstein-Barr virus, Human cytomegalovirus, Human herpesvirus, type 8, Human papillomavirus, BK virus, JC virus, Smallpox, Hepatitis B virus, Human bocavirus, Parvovirus B19, Human astrovirus, Norwalk virus, coxsackievirus, hepatitis A virus, poliovirus, rhinovirus, Severe acute respiratory syndrome virus, Hepatitis C virus, yellow fever virus, dengue virus, West Nile virus, Rubella virus, Hepatitis E virus, Human immunodeficiency virus (HIV), Influenza virus, Guanarito virus, Junin virus, Lassa virus, Machupo virus, Sabiá virus, Crimean-Congo hemorrhagic fever virus, Ebola virus, Marburg virus, Measles virus, Mumps virus, Parainfluenza virus, Respiratory syncytial virus, Human metapneumovirus, Hendra virus, Nipah virus, Rabies virus, Hepatitis D, Rotavirus, Orbivirus, Coltivirus, or Banna virus.

Certain embodiments of the invention make use of a CRISPR/Cas9 nuclease and guide RNA (gRNA) that together target and selectively edit or destroy viral genomic material. The CRISPR (clustered regularly interspaced short palindromic repeats) is a naturally-occurring element of the bacterial immune system that protects bacteria from phage infection. The guide RNA localizes the CRISPR/Cas9 complex to a viral target sequence. Binding of the complex localizes the Cas9 endonuclease to the viral genomic target sequence causing breaks in the viral genome. In a preferred embodiment, the guide RNA is designed to target multiple sites on the viral genome in order to disrupt viral nucleic acid and reduce the chance that it will functionally recombine.

The invention provides methods for targeted delivery of CRISPR/gRNA/Cas9 complex or other therapeutic agents into a cell (including entire tissues) that is infected by a virus. The CRISPR/gRNA/Cas9 complexes of the invention can be delivered by viral, non-viral or other vectors. Viral vectors include retrovirus, lentivirus, adenovirus, herpesvirus, poxvirus, alphavirus, vaccinia virus or adeno-associated viruses. Delivery can also be accomplished by non-viral vectors, such as nanoparticles, cationic lipids, cationic polymers, metallic nanoparticles, nanorods, liposomes, micelles, microbubbles, cell-penetrating peptides, or liposheres. Some non-viral vectors may be coated with polyethyleneglycol (PEG) to reduce the opsonization and aggregation of non-viral vectors and minimize the clearance by the reticuloendothelial system, leading to a prolonged circulation lifetime after intravenous administration. Aspects of the invention provide for the application of energy to delivery vectors for increased tissue-permeabilizing effects (e.g., ultrasound). The invention contemplates both systemic and localized delivery.

Aspects of the invention allow for CRISPR/gRNA/Cas9 complexes to be designed to target viral genomic material and not genomic material of the host. Latent viruses may be, for example, human immunodeficiency virus, human T-cell leukemia virus, Epstein-Barr virus, human cytomegalovirus, human herpesviruses 6 and 7, herpes simplex virus types 1 and 2, varicella-zoster virus, measles virus, or human papovaviruses. Aspects of the invention allow for CRISPR/gRNA/Cas9 complexes to be designed to target any virus, latent or active.

The presented methods allow for viral genome editing or destruction, which results in the inability of the virus to proliferate and/or induces apoptosis in infected cells, with no observed cytotoxicity to non-infected cells. Aspects of the invention involve providing a CRISPR/gRNA/Cas9 complex that selectively targets viral genomic material (DNA or RNA), delivering the CRISPR/gRNA/Cas9 complex to a cell containing the viral genome, and cutting the viral genome in order to incapacitate the virus. The presented methods allows for treatment targeted disruption of viral genomic function or, in a preferred embodiment, digestion of viral nucleic acid via multiple breaks caused by targeting multiple sites for endonuclease action in the viral genome. Aspects of the invention provide for transfection of a CRISPR/gRNA/Cas9 complex cocktail to completely suppress cell proliferation and/or induce apoptosis in infected cells. Additional aspects and advantages of the invention will be apparent upon consideration of the following detailed description thereof.

Aspects of the invention provide a composition for treating a viral infection. The composition includes a vector comprising a gene for a nuclease, a sequence that targets the nuclease to a genome of a virus, and a promoter that promotes transcription from the vector within cells of a specific type. The composition may be used to treat an infection by a varicella zoster virus, i.e., may be used to treat or prevent shingles or postherpetic neuralgia. In some embodiments, the cells are nerve cells and the promoter causes the expression of the genes selectively within the nerve cells. The promoter may be, for example, a cytomegalovirus promoter, a Rous sarcoma virus promoter, or a platelet-derived growth factor (PGDF) promoter. In certain embodiments, the virus is a varicella zoster virus. The sequence may be designed to target a regulatory element in the genome of the virus and preferably lacks any exact match in a human genome. The nuclease may be a cas9 endonuclease. In some embodiments, the sequence is within a clustered regularly interspaced short palindromic repeats (CRISPR) region within the vector, and the CRISPR region encodes a plurality of guide RNAs that match a plurality of targets within the genome of the virus. A promoter may be used that promotes transcription within the peripheral nervous system. Any suitable vector such as an adenoviral vector, a rAAV-based vector, or a plasmid may be used.

BRIEF DESCRIPTION OF THE DRAWINGS

(FIG. 1A) Scheme of CRISPR/Cas plasmids, adapted from Cong L et al. (2013) Multiplex Genome Engineering Using CRISPR/Cas Systems. Science 339:819-823. (FIG. 1B) Effect of oriP on transfection efficiency in Raji cells. Both Cas9 and Cas9-oriP plasmids have a scrambled guide RNA. (FIG. 1C) CRISPR guide RNA targets along the EBV reference genome. Green, red and blue represent three different target sequence categories.

(FIG. 2A) Genome context around guide RNA sgEBV2 and PCR primer locations. (FIG. 2B) Large deletion induced by sgEBV2. Lane 1-3 are before, 5 days after, and 7 days after sgEBV2 treatment, respectively. (FIG. 2C) Genome context around guide RNA sgEBV3/4/5 and PCR primer locations. (FIG. 2D) Large deletions induced by sgEBV3/5 and sgEBV4/5. Lane 1 and 2 are 3F/5R PCR amplicons before and 8 days after sgEBV3/5 treatment. Lane 3 and 4 are 4F/5R PCR amplicons before and 8 days after sgEBV4/5 treatment. (FIGS. 2E and F) Sanger sequencing confirmed genome cleavage and repair ligation 8 days after sgEBV3/5 (FIG. 2E) and sgEBV4/5 (FIG. 2F) treatment. Blue and white background highlights the two ends before repair ligation.

(FIG. 3A) Cell proliferation curves after different CRISPR treatments. Five independent sgEBV1-7 treatments are shown here. (FIGS. 3B-D) Flow cytometry scattering signals before (FIG. 3B), 5 days after (FIG. 3C) and 8 days after (FIG. 3D) sgEBV1-7 treatments. (FIG. 3E-G) Annexin V Alexa647 and DAPI staining results before (FIG. 3E), 5 days after (FIG. 3F) and 8 days after (FIG. 3G) sgEBV1-7 treatments. Blue and red correspond to subpopulation P3 and P4 in (FIGS. 3B-D). (FIGS. 3H and I) Microscopy revealed apoptotic cell morphology after sgEBV1-7 treatment. (FIGS. 3J-M) Nuclear morphology before (FIG. 3J) and after (FIGS. 3K-M) sgEBV1-7 treatment.

(FIG. 4A) EBV load after different CRISPR treatments by digital PCR. Cas9 and Cas9-oriP had two replicates, and sgEBV1-7 had 5 replicates. (FIGS. 4B and C) Microscopy of captured single cells for whole-genome amplification. (FIG. 4D) Histogram of EBV quantitative PCR Ct values from single cells before treatment. (FIG. 4E) Histogram of EBV quantitative PCR Ct values from single live cells 7 days after sgEBV1-7 treatment. Red dash lines in (FIG. 4D) and (FIG. 4E) represent Ct values of one EBV genome per cell.

DETAILED DESCRIPTION

Figure 9:
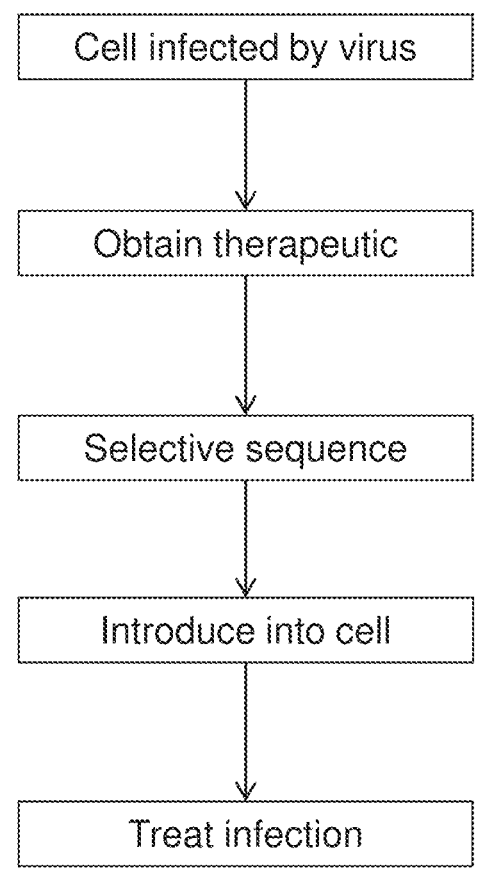
FIG. 9 diagrams a method of the invention.
Figure 12:
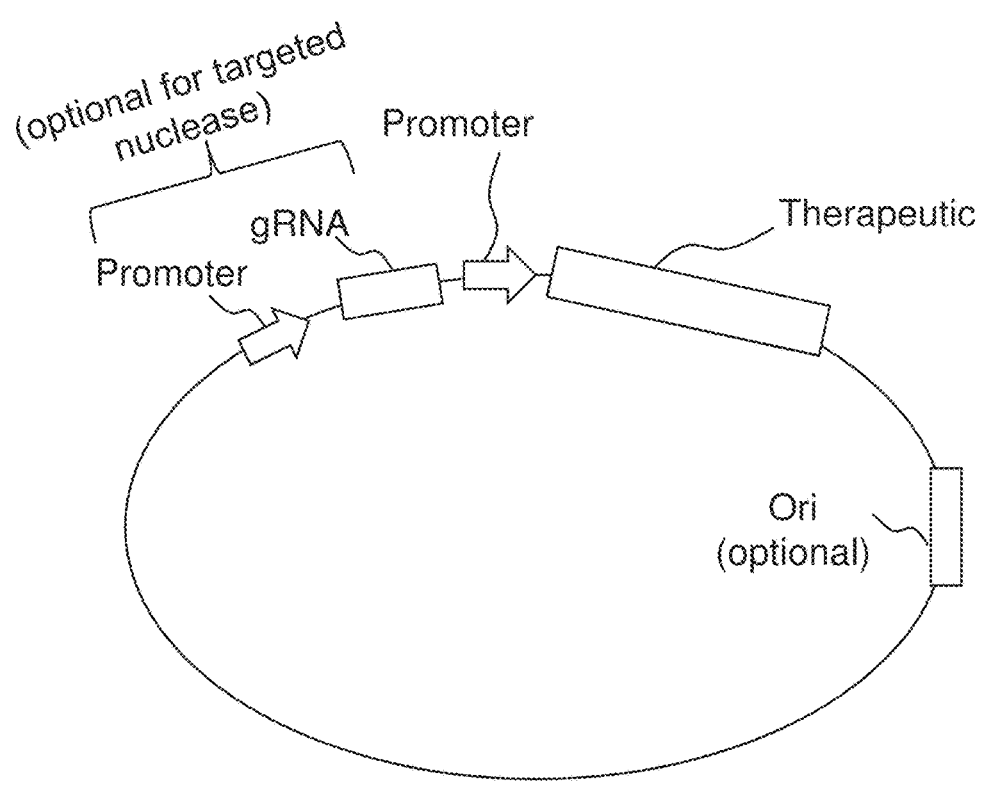
FIG. 12 shows a composition according to certain embodiments.

The invention generally relates to compositions and methods for delivery of therapies targeting viral infection. FIG. 9 diagrams a method of the invention. FIG. 12 shows a composition according to certain embodiments. In some embodiments, the composition includes a vector such as a plasmid that includes at least a gene for a therapeutic (e.g., nuclease or apoptosis-related gene) and a viral-driven promoter as shown in FIG. 12. The composition may optionally include one or more of a guide RNA, other promoters, replication origin, others, or a combination thereof. This invention provides methods and compositions that to allow effective delivery of nucleases or other cytotoxic elements to cells of interest. Methods and compositions are provided for targeted delivery of antiviral therapeutics into cells of interest using, for example, viral vectors such as adenovirus, AAV, and replication incompetent HSV. These and other delivery systems can be used as vehicles to deliver DNA vectors encoding a nuclease or a cell-killing gene. These delivery methods can also be used to deliver naked DNA or RNA, protein products, plasmids containing a promoter that is active only in a latent viral state which drives a cell-killing gene, or other therapeutic agents. Methods and compositions of the invention are designed to specifically target virus and virus-infected cells.

One of the treatments contemplated by the invention is the use of nucleases to target viral genomes. In some embodiments, the invention involves delivering a nuclease into a cell of interest. Nucleases have the ability to incapacitate or disrupt latent viruses within a cell by systematically causing deletions in the viral genome, thereby reducing the ability for the viral genome to replicate itself. In embodiments, the treatment comprises CRISPR/Cas and guided RNA complexes, which cause insertions, deletions, or rearrangements within the viral genome in order to incapacitate or destroy the virus.

The invention generally relates to compositions and methods for selectively treating viral infections using a guided nuclease system. Methods of the invention are used to incapacitate or disrupt viral nucleic acid within a cell through nuclease activity such as single- or double-stranded breaks, cleavage, digestion, or editing. Methods of the invention may be used for systematically causing large or repeated deletions in the genome, reducing the probability of reconstructing the full genome.

i. Treating Infected Cell

FIG. 9 diagrams a method of treating a cell infected with a virus. Methods of the invention are applicable to in vivo treatment of patients and may be used to treat any cell infected with a virus such as by initiating apoptosis in the infected cells or by digesting genes of virus associated with a latent viral infection. Methods may be used in vitro, e.g., to prepare or treat a cell culture or cell sample. When used in vivo, the cell may be any suitable germ line or somatic cell and compositions of the invention may be delivered to specific parts of a patient's body or be delivered systemically. If delivered systemically, it may be preferable to include within compositions of the invention tissue-specific promoters. For example, if a patient has a latent viral infection that is localized to the liver, hepatic tissue-specific promotors may be included in a plasmid or viral vector that codes for a targeted nuclease.

ii. Therapeutic

Methods and compositions of the invention can be used to selectively cause the death of cells that are infected or to selectively target a virus without interfering with the infected cell.

1. Apoptotic

In some embodiments, the invention provides methods and therapeutics that can be used to cause the death of host cells but only those cells that are infected. For example, the treatment can include delivering a gene for a protein that causes cell death, where the gene is under control of a viral regulatory element such as a promoter from the genome of the infecting virus or the gene is encoded in a vector that includes a viral origin of replication. Where the virus is present, the gene will be expressed and the gene product will cause the death of the cell. The gene can code for a protein important in apoptosis, or the gene can code for a nuclease that digests the host genome.

The therapeutic may be provided encoded within a vector, in which the vector also encodes a sequence that causes the therapeutic to be expressed within a cell that is infected by a virus. The sequence may be a regulatory element (e.g., a promoter and an origin of replication) from the genome of the virus. The therapeutic may provide a mechanism that selectively causes death of virus-infected cells. For example, a protein may be used that restores a deficient apoptotic pathway in the cell. The gene may be, for example, BAX, BAK, BCL-2, or alpha-hemolysin. Preferably, the therapeutic induces apoptosis in the cell that is infected by the virus and does not induce apoptosis in an uninfected cell.

In cases where a small number of cells are infected and it would suffice to ablate the entire cell (as well as the latent viral genome), an aspect of the invention contemplates administration of a vector containing a promoter which is active in the latent viral state, wherein the promoter drives a cell-killing gene. HSV is a particularly interesting target for this approach as it has been estimated that only thousands to tens of thousands neurons are latently infected. See Hoshino et al., 2008, The number of herpes simplex virus-infected neurons and the number of viral genome copies per neuron correlate with latent viral load in ganglia, Virology 372(1):56-63, incorporated by reference. Examples of cell-killing genes include apoptosis effectors such as BAX and BAK and proteins that destroy the integrity of the cell or mitochondrial membrane, such as alpha hemolysin. (Bayles, "Bacterial programmed cell death: making sense of a paradox," Nature Reviews Microbiology 12 pp. 63-69 (2014)). Having a promoter that is only activated in latently infected cells could be used not only in this context but also be used to increase selectivity of nuclease therapy by making activity specific to infected cells; an example of such a promoter is Latency-Associated Promoter 1, or "LAP1". (Preston and Efstathiou, "Molecular Basis of HSV Latency and Reactivation", in Human Herpesviruses: Biology, Therapy and Immunoprophylaxis 2007.)

In some embodiments, the invention provides a composition that includes a viral vector, plasmid, or other coding nucleic acid that encodes at least one gene that promotes apoptosis and at least one promoter associated a viral genome. Apoptosis regulator Bcl-2 is a family of proteins that govern mitochondrial outer membrane permeabilization (MOMP) and include pro-apoptotic proteins such as Bax, BAD, Bak, Bok, Bcl-rambo, Bcl-xs and BOK/Mtd.

Apoptosis regulator BAX, also known as bcl-2-like protein 4, is a protein that in humans is encoded by the BAX gene. BAX is a member of the Bcl-2 gene family. This protein forms a heterodimer with BCL2, and functions as an apoptotic activator. This protein is reported to interact with, and increase the opening of, the mitochondrial voltage-dependent anion channel (VDAC), which leads to the loss in membrane potential and the release of cytochrome c.

Bcl-2 homologous antagonist/killer is a protein that in humans is encoded by the BAK1 gene on chromosome 6. This protein localizes to mitochondria, and functions to induce apoptosis. It interacts with and accelerates the opening of the mitochondrial voltage-dependent anion channel, which leads to a loss in membrane potential and the release of cytochrome c.

Human genes encoding proteins that belong to this family include: BAK1, BAX, BCL2, BCL2A1, BCL2L1, BCL2L2, BCL2L10, BCL2L13, BCL2L14, BOK, and MCL1.

2. Antiviral

Methods of the invention include using a programmable or targetable nuclease to specifically target viral nucleic acid for destruction. Any suitable targeting nuclease can be used including, for example, zinc-finger nucleases (ZFNs), transcription activator-like effector nucleases (TALENs), clustered regularly interspaced short palindromic repeat (CRISPR) nucleases, meganucleases, other endo- or exo-nucleases, or combinations thereof. See Schiffer, 2012, Targeted DNA mutagenesis for the cure of chronic viral infections, J Virol 88(17):8920-8936, incorporated by reference.

CRISPR methodologies employ a nuclease, CRISPR-associated (Cas9), that complexes with small RNAs as guides (gRNAs) to cleave DNA in a sequence-specific manner upstream of the protospacer adjacent motif (PAM) in any genomic location. CRISPR may use separate guide RNAs known as the crRNA and tracrRNA. These two separate RNAs have been combined into a single RNA to enable site-specific mammalian genome cutting through the design of a short guide RNA. Cas9 and guide RNA (gRNA) may be synthesized by known methods. Cas9/guide-RNA (gRNA) uses a non-specific DNA cleavage protein Cas9, and an RNA oligo to hybridize to target and recruit the Cas9/gRNA complex. See Chang et al., 2013, Genome editing with RNA-guided Cas9 nuclease in zebrafish embryos, Cell Res 23:465-472; Hwang et al., 2013, Efficient genome editing in zebrafish using a CRISPR-Cas system, Nat. Biotechnol 31:227-229; Xiao et al., 2013, Chromosomal deletions and inversions mediated by TALENS and CRISPR/Cas in zebrafish, Nucl Acids Res 1-11.

CRISPR(Clustered Regularly Interspaced Short Palindromic Repeats) is found in bacteria and is believed to protect the bacteria from phage infection. It has recently been used as a means to alter gene expression in eukaryotic DNA, but has not been proposed as an anti-viral therapy or more broadly as a way to disrupt genomic material. Rather, it has been used to introduce insertions or deletions as a way of increasing or decreasing transcription in the DNA of a targeted cell or population of cells. See for example, Horvath et al., Science (2010) 327:167-170; Terns et al., Current Opinion in Microbiology (2011) 14:321-327; Bhaya et al Annu Rev Genet (2011) 45:273-297; Wiedenheft et al. Nature (2012) 482:331-338); Jinek M et. al. Science (2012) 337:816-821; Cong L et al. Science (2013) 339:819-823; Jinek M et al. (2013) eLife 2:e00471; Mali P et. al. (2013) Science 339:823-826; Qi L S et al. (2013) Cell 152:1173-1183; Gilbert L A et al. (2013) Cell 154:442-451; Yang H et al. (2013) Cell 154:1370-1379; and Wang H et al. (2013) Cell 153:910-918). Additionally, in the U.S. Provisional Application 62/005,395 it has been proposed as an anti-viral therapy or more broadly as a way to disrupt genomic material.

In an aspect of the invention, the Cas9 endonuclease causes a double strand break in at least two locations in the genome. These two double strand breaks cause a fragment of the genome to be deleted. Even if viral repair pathways anneal the two ends, there will still be a deletion in the genome. One or more deletions using the mechanism will incapacitate the viral genome. The result is that the host cell will be free of viral infection.

In embodiments of the invention, nucleases cleave the genome of the target virus. A nuclease is an enzyme capable of cleaving the phosphodiester bonds between the nucleotide subunits of nucleic acids. Endonucleases are enzymes that cleave the phosphodiester bond within a polynucleotide chain. Some, such as Deoxyribonuclease I, cut DNA relatively nonspecifically (without regard to sequence), while many, typically called restriction endonucleases or restriction enzymes, cleave only at very specific nucleotide sequences. In a preferred embodiment of the invention, the Cas9 nuclease is incorporated into the compositions and methods of the invention, however, it should be appreciated that any nuclease may be utilized.

In preferred embodiments of the invention, the Cas9 nuclease is used to cleave the genome. The Cas9 nuclease is capable of creating a double strand break in the genome. The Cas9 nuclease has two functional domains: RuvC and HNH, each cutting a different strand. When both of these domains are active, the Cas9 causes double strand breaks in the genome.

In some embodiments of the invention, insertions into the genome can be designed to cause incapacitation, or altered genomic expression. Additionally, insertions/deletions are also used to introduce a premature stop codon either by creating one at the double strand break or by shifting the reading frame to create one downstream of the double strand break. Any of these outcomes of the NHEJ repair pathway can be leveraged to disrupt the target gene. The changes introduced by the use of the CRISPR/gRNA/Cas9 system are permanent to the genome.

In some embodiments of the invention, at least one insertion is caused by the CRISPR/gRNA/Cas9 complex. In a preferred embodiment, numerous insertions are caused in the genome, thereby incapacitating the virus. In an aspect of the invention, the number of insertions lowers the probability that the genome may be repaired.

In some embodiments of the invention, at least one deletion is caused by the CRISPR/gRNA/Cas9 complex. In a preferred embodiment, numerous deletions are caused in the genome, thereby incapacitating the virus. In an aspect of the invention, the number of deletions lowers the probability that the genome may be repaired. In a highly-preferred embodiment, the CRISPR/Cas9/gRNA system of the invention causes significant genomic disruption, resulting in effective destruction of the viral genome, while leaving the host genome intact.

TALENs uses a nonspecific DNA-cleaving nuclease fused to a DNA-binding domain that can be to target essentially any sequence. For TALEN technology, target sites are identified and expression vectors are made. Linearized expression vectors (e.g., by NotI) may be used as template for mRNA synthesis. A commercially available kit may be use such as the mMESSAGE mMACHINE SP6 transcription kit from Life Technologies (Carlsbad, Calif.). See Joung & Sander, 2013, TALENs: a wideliy applicable technology for targeted genome editing, Nat Rev Mol Cell Bio 14:49-55.

TALENs and CRISPR methods provide one-to-one relationship to the target sites, i.e. one unit of the tandem repeat in the TALE domain recognizes one nucleotide in the target site, and the crRNA, gRNA, or sgRNA of CRISPR/Cas system hybridizes to the complementary sequence in the DNA target. Methods can include using a pair of TALENs or a Cas9 protein with one gRNA to generate double-strand breaks in the target. The breaks are then repaired via non-homologous end joining or homologous recombination (HR).

Figure 8:
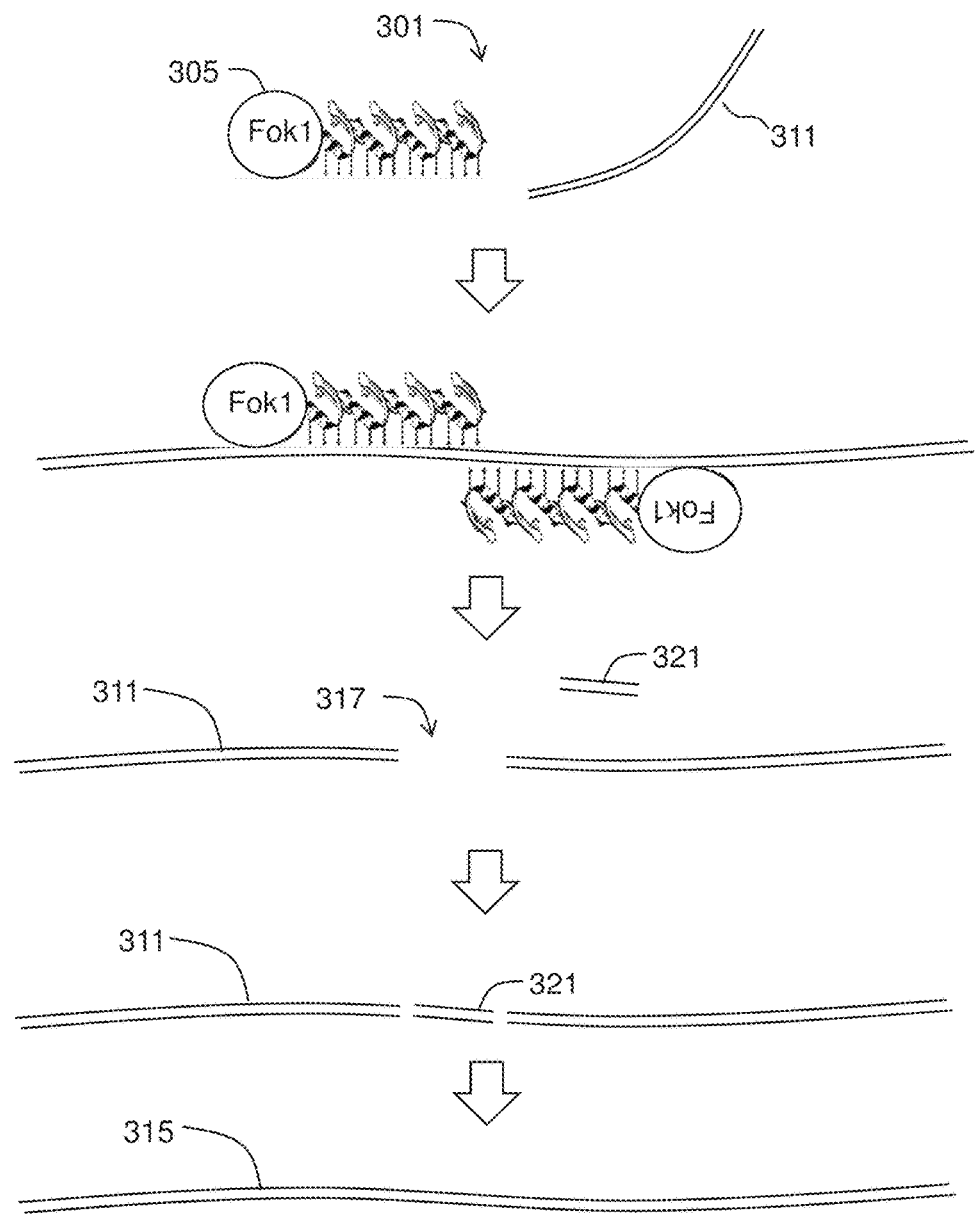
FIG. 8 shows the use of ZFNs.

FIG. 8 shows ZFN being used to cut viral nucleic acid. Briefly, the ZFN method includes introducing into the infected host cell at least one vector (e.g., RNA molecule) encoding a targeted ZFN 305 and, optionally, at least one accessory polynucleotide. See, e.g., U.S. Pub. 2011/0023144 to Weinstein, incorporated by reference The cell includes target sequence 311. The cell is incubated to allow expression of the ZFN 305, wherein a double-stranded break 317 is introduced into the targeted chromosomal sequence 311 by the ZFN 305. In some embodiments, a donor polynucleotide or exchange polynucleotide 321 is introduced. Swapping a portion of the viral nucleic acid with irrelevant sequence can fully interfere transcription or replication of the viral nucleic acid. Target DNA 311 along with exchange polynucleotide 321 may be repaired by an error-prone non-homologous end joining DNA repair process or a homology-directed DNA repair process.

Typically, a ZFN comprises a DNA binding domain (i.e., zinc finger) and a cleavage domain (i.e., nuclease) and this gene may be introduced as mRNA (e.g., 5' capped, polyadenylated, or both). Zinc finger binding domains may be engineered to recognize and bind to any nucleic acid sequence of choice. See, e.g., Qu et al., 2013, Zinc-finger-nucleases mediate specific and efficient excision of HIV-1 proviral DAN from infected and latently infected human T cells, Nucl Ac Res 41(16):7771-7782, incorporated by reference. An engineered zinc finger binding domain may have a novel binding specificity compared to a naturally-occurring zinc finger protein. Engineering methods include, but are not limited to, rational design and various types of selection. A zinc finger binding domain may be designed to recognize a target DNA sequence via zinc finger recognition regions (i.e., zinc fingers). See for example, U.S. Pat. Nos. 6,607,882; 6,534,261 and 6,453,242, incorporated by reference. Exemplary methods of selecting a zinc finger recognition region may include phage display and two-hybrid systems, and are disclosed in U.S. Pat. No. 5,789,538; U.S. Pat. No. 5,925,523; U.S. Pat. No. 6,007,988; U.S. Pat. No. 6,013,453; U.S. Pat. No. 6,410,248; U.S. Pat. No. 6,140,466; U.S. Pat. No. 6,200,759; and U.S. Pat. No. 6,242,568, each of which is incorporated by reference.

A ZFN also includes a cleavage domain. The cleavage domain portion of the ZFNs may be obtained from any suitable endonuclease or exonuclease such as restriction endonucleases and homing endonucleases. See, for example, Belfort & Roberts, 1997, Homing endonucleases: keeping the house in order, Nucleic Acids Res 25(17):3379-3388. A cleavage domain may be derived from an enzyme that requires dimerization for cleavage activity. Two ZFNs may be required for cleavage, as each nuclease comprises a monomer of the active enzyme dimer. Alternatively, a single ZFN may comprise both monomers to create an active enzyme dimer. Restriction endonucleases present may be capable of sequence-specific binding and cleavage of DNA at or near the site of binding. Certain restriction enzymes (e.g., Type IIS) cleave DNA at sites removed from the recognition site and have separable binding and cleavage domains. For example, the Type IIS enzyme FokI, active as a dimer, catalyzes double-stranded cleavage of DNA, at 9 nucleotides from its recognition site on one strand and 13 nucleotides from its recognition site on the other. The FokI enzyme used in a ZFN may be considered a cleavage monomer. Thus, for targeted double-stranded cleavage using a FokI cleavage domain, two ZFNs, each comprising a FokI cleavage monomer, may be used to reconstitute an active enzyme dimer. See Wah, et al., 1998, Structure of FokI has implications for DNA cleavage, PNAS 95:10564-10569; U.S. Pat. No. 5,356,802; U.S. Pat. No. 5,436,150; U.S. Pat. No. 5,487,994; U.S. Pub. 2005/0064474; U.S. Pub. 2006/0188987; and U.S. Pub. 2008/0131962, each incorporated by reference.

Virus targeting using ZFN may include introducing at least one donor polynucleotide comprising a sequence into the cell. A donor polynucleotide preferably includes the sequence to be introduced flanked by an upstream and downstream sequence that share sequence similarity with either side of the site of integration in the chromosome. The upstream and downstream sequences in the donor polynucleotide are selected to promote recombination between the chromosomal sequence of interest and the donor polynucleotide. Typically, the donor polynucleotide will be DNA. The donor polynucleotide may be a DNA plasmid, a bacterial artificial chromosome (BAC), a yeast artificial chromosome (YAC), a viral vector, a linear piece of DNA, a PCR fragment, a naked nucleic acid, and may employ a delivery vehicle such as a liposome. The sequence of the donor polynucleotide may include exons, introns, regulatory sequences, or combinations thereof. The double stranded break is repaired via homologous recombination with the donor polynucleotide such that the desired sequence is integrated into the chromosome. In the ZFN-mediated process for modifying a chromosomal sequence, a double stranded break introduced into the chromosomal sequence by the ZFN is repaired, via homologous recombination with the exchange polynucleotide, such that the sequence in the exchange polynucleotide may be exchanged with a portion of the chromosomal sequence. The presence of the double stranded break facilitates homologous recombination and repair of the break. The exchange polynucleotide may be physically integrated or, alternatively, the exchange polynucleotide may be used as a template for repair of the break, resulting in the exchange of the sequence information in the exchange polynucleotide with the sequence information in that portion of the chromosomal sequence. Thus, a portion of the viral nucleic acid may be converted to the sequence of the exchange polynucleotide. ZFN methods can include using a vector to deliver a nucleic acid molecule encoding a ZFN and, optionally, at least one exchange polynucleotide or at least one donor polynucleotide to the infected cell.

Meganucleases are endodeoxyribonucleases characterized by a large recognition site (double-stranded DNA sequences of 12 to 40 base pairs); as a result this site generally occurs only once in any given genome. For example, the 18-base pair sequence recognized by the I-SceI meganuclease would on average require a genome twenty times the size of the human genome to be found once by chance (although sequences with a single mismatch occur about three times per human-sized genome). Meganucleases are therefore considered to be the most specific naturally occurring restriction enzymes. Meganucleases can be divided into five families based on sequence and structure motifs: LAGLIDADG, GIY-YIG, HNH, His-Cys box and PD-(D/E)XK. The most well studied family is that of the LAGLIDADG proteins, which have been found in all kingdoms of life, generally encoded within introns or inteins although freestanding members also exist. The sequence motif, LAGLIDADG, represents an essential element for enzymatic activity. Some proteins contained only one such motif, while others contained two; in both cases the motifs were followed by ~75-200 amino acid residues having little to no sequence similarity with other family members. Crystal structures illustrates mode of sequence specificity and cleavage mechanism for the LAGLIDADG family: (i) specificity contacts arise from the burial of extended β-strands into the major groove of the DNA, with the DNA binding saddle having a pitch and contour mimicking the helical twist of the DNA; (ii) full hydrogen bonding potential between the protein and DNA is never fully realized; (iii) cleavage to generate the characteristic 4-nt 3'-OH overhangs occurs across the minor groove, wherein the scissile phosphate bonds are brought closer to the protein catalytic core by a distortion of the DNA in the central "4-base" region; (iv) cleavage occurs via a proposed two-metal mechanism, sometimes involving a unique "metal sharing" paradigm; (v) and finally, additional affinity and/or specificity contacts can arise from "adapted" scaffolds, in regions outside the core α/β fold. See Silva et al., 2011, Meganucleases and other tools for targeted genome engineering, Curr Gene Ther 11(1):11-27, incorporated by reference.

In some embodiments of the invention, a template sequence is inserted into the genome. In order to introduce nucleotide modifications to genomic DNA, a DNA repair template containing the desired sequence must be present during HDR. The DNA template is normally transfected into the cell along with the gRNA/Cas9. The length and binding position of each homology arm is dependent on the size of the change being introduced. In the presence of a suitable template, HDR can introduce specific nucleotide changes at the Cas9 induced double strand break.

Some embodiments of the invention may utilize modified version of a nuclease. Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. Similar to the inactive dCas9 (RuvC- and HNH-), a Cas9 nickase is still able to bind DNA based on gRNA specificity, though nickases will only cut one of the DNA strands. The majority of CRISPR plasmids are derived from S. pyogenes and the RuvC domain can be inactivated by a D10A mutation and the HNH domain can be inactivated by an H840A mutation.

A single-strand break, or nick, is normally quickly repaired through the HDR pathway, using the intact complementary DNA strand as the template. However, two proximal, opposite strand nicks introduced by a Cas9 nickase are treated as a double strand break, in what is often referred to as a 'double nick' or 'dual nickase' CRISPR system. A double-nick induced double strain break can be repaired by either NHEJ or HDR depending on the desired effect on the gene target. At these double strain breaks, insertions and deletions are caused by the CRISPR/Cas9 complex. In an aspect of the invention, a deletion is caused by positioning two double strand breaks proximate to one another, thereby causing a fragment of the genome to be deleted.

iii. Targeting Moiety

A nuclease may use the targeting specificity of a gRNA in order to act. As discussed below, guide RNAs or single guide RNAs are specifically designed to target a virus genome.

A CRISPR/Cas9 gene editing complex of the invention works optimally with a guide RNA that targets the viral genome. Guide RNA (gRNA) or single guide RNA (sgRNA) leads the CRISPR/Cas9 complex to the viral genome in order to cause viral genomic disruption. In an aspect of the invention, CRISPR/Cas9/gRNA complexes are designed to target specific viruses within a cell. It should be appreciated that any virus can be targeted using the composition of the invention. Identification of specific regions of the virus genome aids in development and designing of CRISPR/Cas9/gRNA complexes.

In an aspect of the invention, the CRISPR/Cas9/gRNA complexes are designed to target latent viruses within a cell. Once transfected within a cell, the CRISPR/Cas9/gRNA complexes cause repeated insertions or deletions to render the genome incapacitated, or due to number of insertions or deletions, the probability of repair is significantly reduced.

Figure 1A:
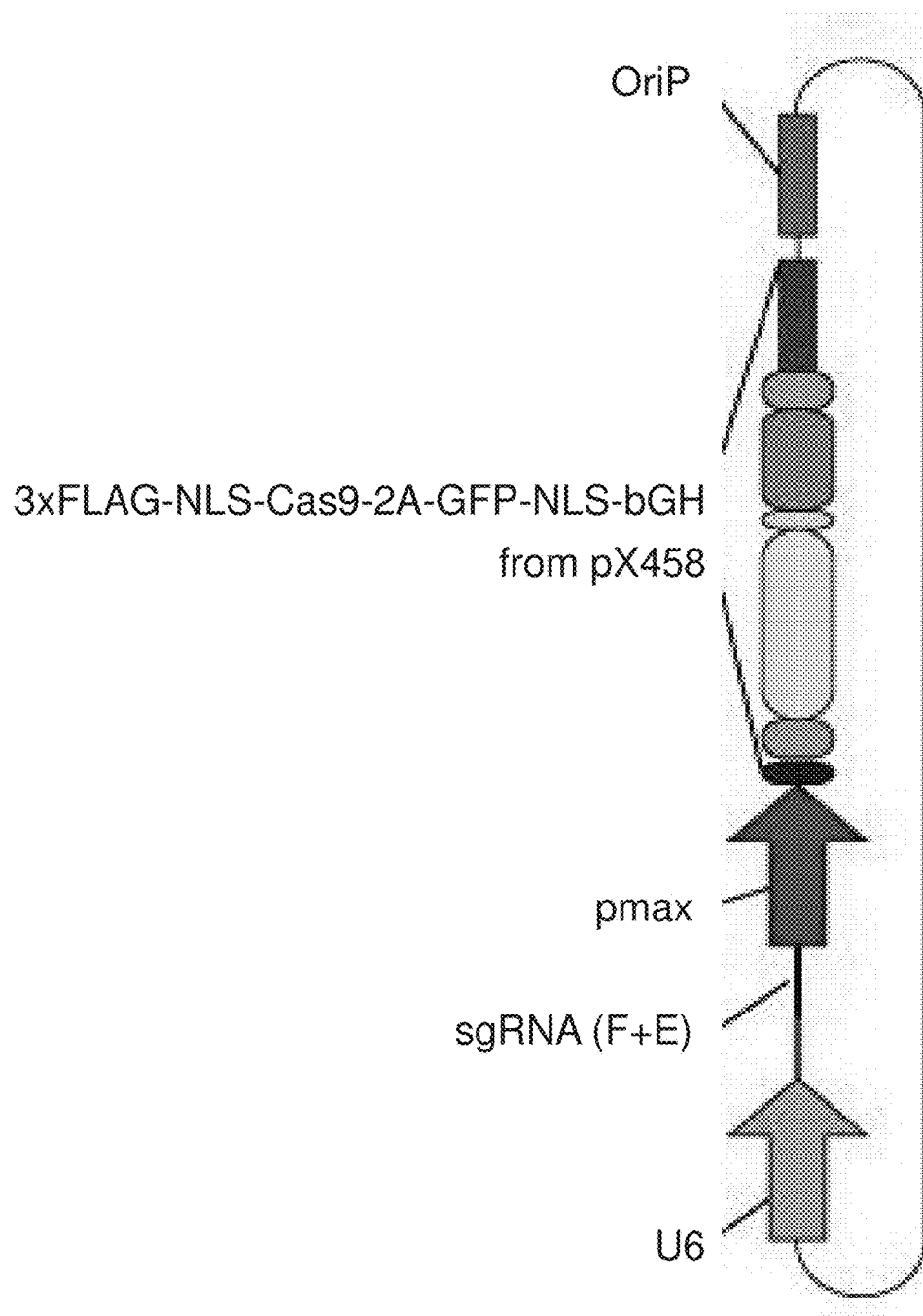
FIGS. 1A-1C represent EBV-targeting CRISPR/Cas9 designs.

As an example, the Epstein-Barr virus (EBV), also called human herpesvirus 4 (HHV-4) is inactivated in cells by a CRISPR/Cas9/gRNA complex of the invention. EBV is a virus of the herpes family, and is one of the most common viruses in humans. The virus is approximately 122 nm to 180 nm in diameter and is composed of a double helix of DNA wrapped in a protein capsid. In this example, the Raji cell line serves as an appropriate in vitro model. The Raji cell line is the first continuous human cell line from hematopoietic origin and cell lines produce an unusual strain of Epstein-Barr virus while being one of the most extensively studied EBV models. To target the EBV genomes in the Raji cells, a CRISPR/Cas9 complex with specificity for EBV is needed. The design of EBV-targeting CRISPR/Cas9 plasmids consisting of a U6 promoter driven chimeric guide RNA (sgRNA) and a ubiquitous promoter driven Cas9 that were obtained from Addgene, Inc. Commercially available guide RNAs and Cas9 nucleases may be used with the present invention. An EGFP marker fused after the Cas9 protein allowed selection of Cas9-positive cells (FIG. 1A).

In an aspect of the invention, guide RNAs are designed, whether or not commercially purchased, to target a specific viral genome. The viral genome is identified and guide RNA to target selected portions of the viral genome are developed and incorporated into the composition of the invention. In an aspect of the invention, a reference genome of a particular strain of the virus is selected for guide RNA design.

Figure 1B:
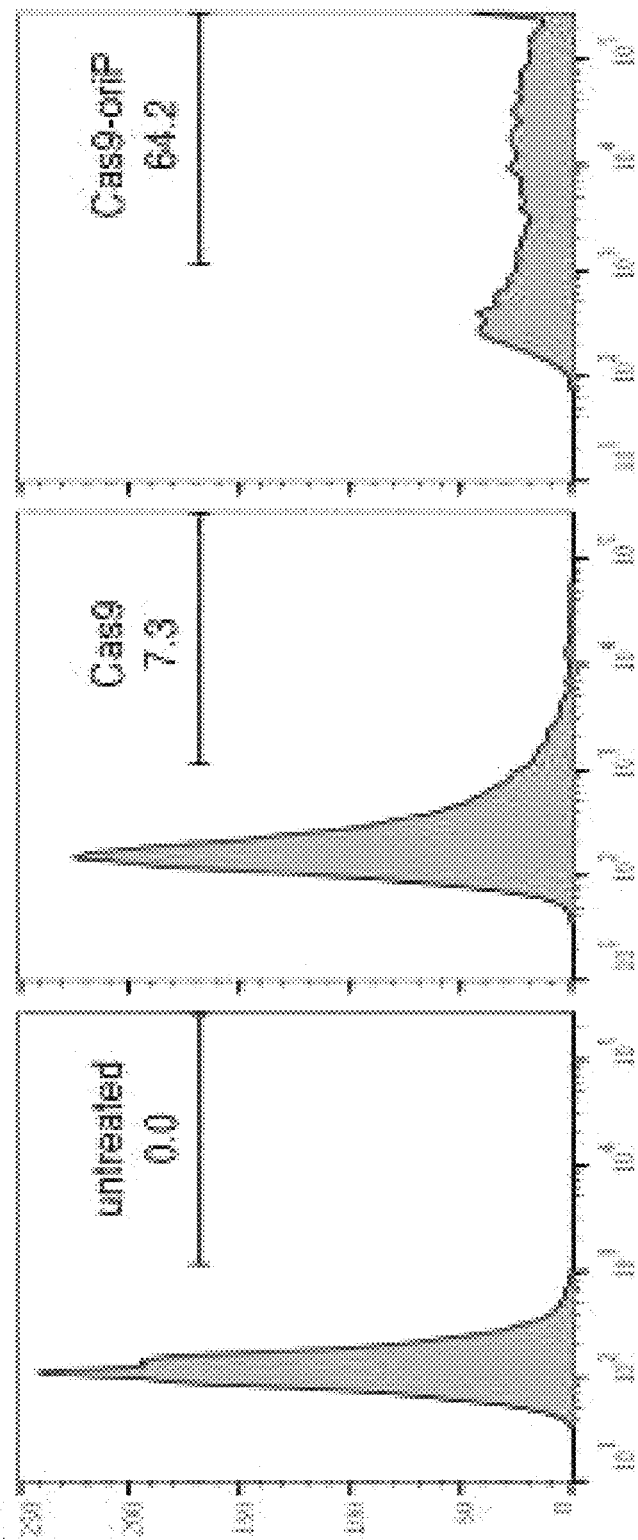
Figure 1C:
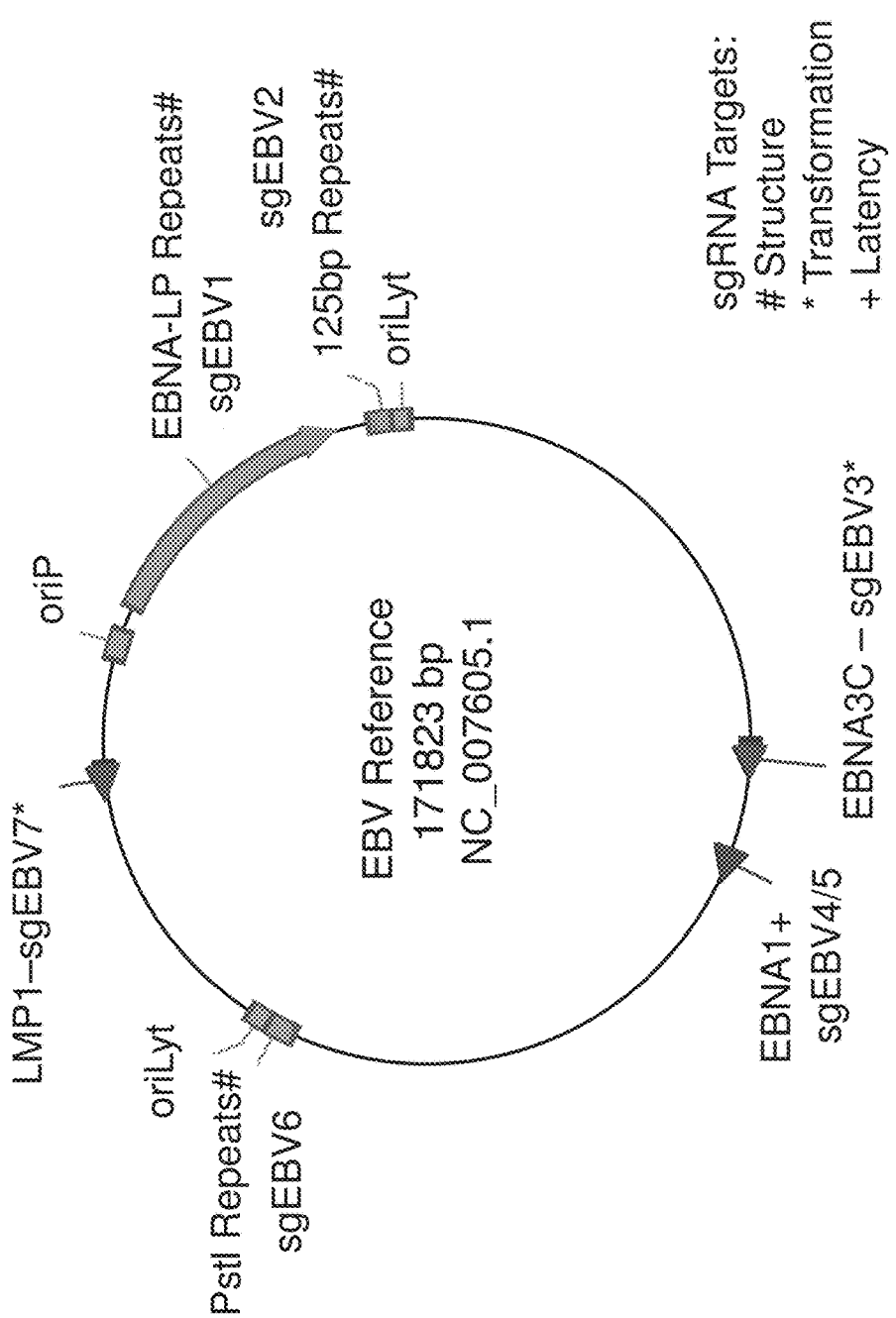

For example, guide RNAs that target the EBV genome are a component of the system in the present example. In relation to EBV, for example, the reference genome from strain B95-8 was used as a design guide. Within a genome of interest, such as EBV, selected regions, or genes are targeted. For example, six regions can be targeted with seven guide RNA designs for different genome editing purposes (FIG. 1C and Table S1).

TABLE S1

Guide RNA target sequences

| | Guide RNA Sequence | |
|---|---|---|
| sgEBV1 | GCCCTGGACCAACCCGGCCC | (SEQ ID NO: 1) |
| sgEBV2 | GGCCGCTGCCCCGCTCCGGG | (SEQ ID NO: 2) |
| sgEBB3 | GGAAGACAATGTGCCGCCA | (SEQ ID NO: 3) |
| sgEBV4 | TCTGGACCAGAAGGCTCCGG | (SEQ ID NO: 4) |
| sgEBV5 | GCTGCCGCGGAGGGTGATGA | (SEQ ID NO: 5) |
| sgEBV6 | GGTGGCCCACCGGGTCCGCT | (SEQ ID NO: 6) |
| sgEBV7 | GTCCTCGAGGGGGCCGTCGC | (SEQ ID NO: 7) |

In relation to EBV, EBNA1 is the only nuclear Epstein-Barr virus (EBV) protein expressed in both latent and lytic modes of infection. While EBNA1 is known to play several important roles in latent infection, EBNA1 is crucial for many EBV functions including gene regulation and latent genome replication. Therefore, guide RNAs sgEBV4 and sgEBV5 were selected to target both ends of the EBNA1 coding region in order to excise this whole region of the genome. These "structural" targets enable systematic digestion of the EBV genome into smaller pieces. EBNA3C and LMP1 are essential for host cell transformation, and guide RNAs sgEBV3 and sgEBV7 were designed to target the 5' exons of these two proteins respectively.

iv. Introduce to Cell

Methods of the invention include introducing into a cell a nuclease and a sequence-specific targeting moiety. The nuclease is targeted to viral nucleic acid by means of the sequence-specific targeting moiety where it then cleaves the viral nucleic acid without interfering with a host genome. Any suitable method can be used to deliver the nuclease to the infected cell or tissue. For example, the nuclease or the gene encoding the nuclease may be delivered by injection, orally, or by hydrodynamic delivery. The nuclease or the gene encoding the nuclease may be delivered to systematic circulation or may be delivered or otherwise localized to a specific tissue type.

Some viral infections affect only a small number of cells, and it may be preferable to employ a targeted delivery approach. It has been estimated that HSV, for example, latently infects on the order of only 20,000 neurons. For this and other viral infections, it may be important to have a treatment that is targeted only to the cells of interest. Increasing the cell affinity and specificity can greatly improve therapeutic delivery efficiency.

The nuclease or gene encoding the nuclease may be modified or programmed to be active under only certain conditions such as by using a tissue-specific promoter so that the encoded nuclease is preferentially or only transcribed in certain tissue types.

In some embodiments, specific CRISPR/Cas9/gRNA complexes are introduced into a cell. A guide RNA is designed to target at least one category of sequences of the viral genome. In addition to latent infections this invention can also be used to control actively replicating viruses by targeting the viral genome before it is packaged or after it is ejected.

Prepackaged GFP-Cas9-adenovirus is available from Vector Biolabs (Philadelphia, Pa.). Various targeting gRNA sequences, such as sequences that target EBV can be packaged to adenovirus lines. The gRNA sequences can be housed together with the CRISPR/Cas9 complex or separately.

In some embodiments, a cocktail of guide RNAs may be introduced into a cell. The guide RNAs are designed to target numerous categories of sequences of the viral genome. By targeting several areas along the genome, the double strand break at multiple locations fragments the genome, lowering the possibility of repair. Even with repair mechanisms, the large deletions render the virus incapacitated.

In some embodiments, several guide RNAs are added to create a cocktail to target different categories of sequences. For example, two, five, seven or eleven guide RNAs may be present in a CRISPR cocktail targeting three different categories of sequences. However, any number of gRNAs may be introduced into a cocktail to target categories of sequences. In preferred embodiments, the categories of sequences are important for genome structure, host cell transformation, and infection latency, respectively.

In some aspects of the invention, in vitro experiments allow for the determination of the most essential targets within a viral genome. For example, to understand the most essential targets for effective incapacitation of a genome, subsets of guide RNAs are transfected into model cells. Assays can determine which guide RNAs or which cocktail is the most effective at targeting essential categories of sequences.

These agents can be delivered either as part of a viral vector (examples further described below), or as naked as DNA or RNA. Naked nucleic acids can be modified to avoid degradation.

Another possibility is to deliver the protein product itself either fused to a signaling molecule or packaged into a vesicle with signaling molecules on surface, or packed into a nanoparticle, vesicle, or attached to a colloid. Examples of this method of delivery have been previously explored in cancer but not applied to local delivery against latent viral infections. (See Alexis et al, "Nanoparticle Technologies for Cancer Therapy" in Drug Delivery, Handbook of Experimental Pharmacology 197, 2010.) Other delivery methods are described in detail below. For HSV and other viruses which are highly localized in terms of which cells and tissues they infect, these therapies might be delivered as a local injection or as a cream.

In other embodiments of the invention, physical approaches can be used to ablate cells that have latent infection, taking advantage of the fact that these are localized in diseases such as HSV. One approach is to image infected cells (for example, using fluorescent markers against viral protein, or against viral genome, or fluorescence proteins induced by viral latency promoters) and then use heat, light, or radio frequency radiation to ablate those cells. Direct contrast agents can also be used towards infected cells. Instead of fluorescence molecules, semiconductor or metallic nanoparticles, colloids, or other structures that interact strongly with light or radio frequency can be used. These can be applied locally with a cream or injections. These substances can potentially take advantage of a cooperative effect, such that infected cells attract multiple particles, thereby having the highest effect. Similar approaches have been used in cancer treatment (See for example Jain et al "Gold nanoparticles as novel agents for cancer therapy," Br J Radiol February 2012 85(1010):101-113). The present invention applies these techniques to treatment of latent viral infection.

In another embodiment, labeled and infected cells can be excised using microsurgery tools such as a fiber optic endoscope, which allows imaging and delivery of radiation in a highly localized manner, with single cell resolution. (See Barretto R P and Schnitzer M J. "In Vivo Optical Microendoscopy for Imaging Cells Lying Deep within Live Tissue." Cold Spring Harb Protoc. 2012(10) and Llewellyn M E, Barretto R P J, Delp S L & Schnitzer M J. (2008) Minimally invasive high-speed imaging of sarcomere contractile dynamics in mice and humans. Nature. 454 784-788).

Figure 2A:
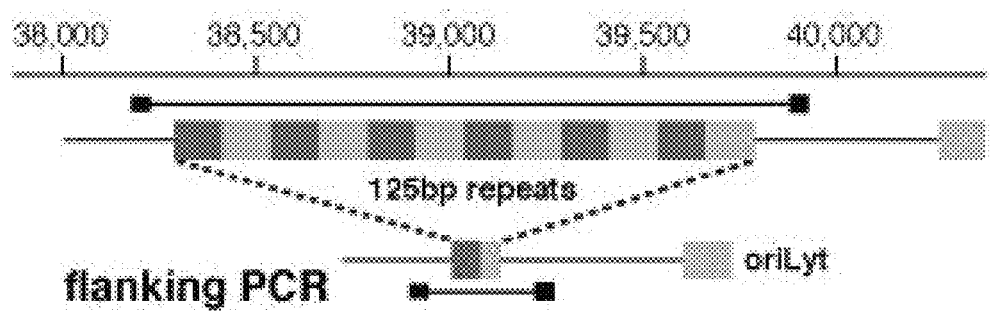
FIGS. 2A-2F represent CRISPR/Cas9 induced large deletions.
Figure 2B:
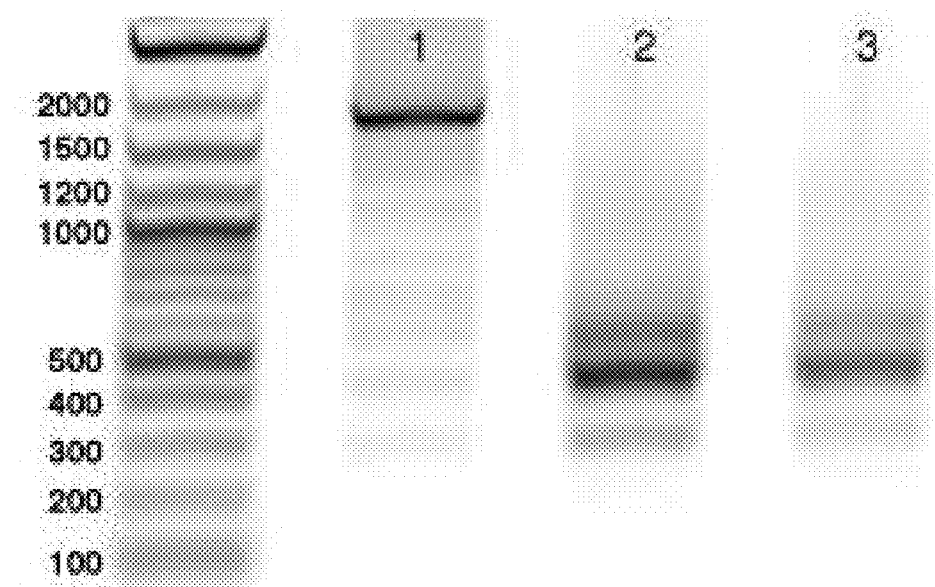

For example, in the case of the EBV genome targeting, seven guide RNAs in the CRISPR cocktail targeted three different categories of sequences which are identified as being important for EBV genome structure, host cell transformation, and infection latency, respectively. To understand the most essential targets for effective EBV treatment, Raji cells were transfected with subsets of guide RNAs. Although sgEBV4/5 reduced the EBV genome by 85%, they could not suppress cell proliferation as effectively as the full cocktail (FIG. 3A). Guide RNAs targeting the structural sequences (sgEBV1/2/6) could stop cell proliferation completely, despite not eliminating the full EBV load (26% decrease). Given the high efficiency of genome editing and the proliferation arrest (FIG. 2), it was suspect that the residual EBV genome signature in sgEBV1/2/6 was not due to intact genomes but to free-floating DNA that has been digested out of the EBV genome, i.e. as a false positive.

Once CRISPR/Cas9/gRNA complexes are constructed, the complexes are introduced into a cell. It should be appreciated that complexes can be introduced into cells in an in vitro model or an in vivo model. In an aspect of the invention, CRISPR/Cas9/gRNA complexes are designed to not leave intact genomes of a virus after transfection and complexes are designed for efficient transfection.

Aspects of the invention allow for CRISPR/Cas9/gRNA to be transfected into cells by various methods, including viral vectors and non-viral vectors. Viral vectors may include retroviruses, lentiviruses, adenoviruses, and adeno-associated viruses. It should be appreciated that any viral vector may be incorporated into the present invention to effectuate delivery of the CRISPR/Cas9/gRNA complex into a cell. Some viral vectors may be more effective than others, depending on the CRISPR/Cas9/gRNA complex designed for digestion or incapacitation. In an aspect of the invention, the vectors contain essential components such as origin of replication, which is necessary for the replication and maintenance of the vector in the host cell.

In an aspect of the invention, viral vectors are used as delivery vectors to deliver the complexes into a cell. Use of viral vectors as delivery vectors are known in the art. See for example U.S. Pub. 2009/0017543 to Wilkes et al., the contents of which are incorporated by reference.

A retrovirus is a single-stranded RNA virus that stores its nucleic acid in the form of an mRNA genome (including the 5' cap and 3' PolyA tail) and targets a host cell as an obligate parasite. In some methods in the art, retroviruses have been used to introduce nucleic acids into a cell. Once inside the host cell cytoplasm the virus uses its own reverse transcriptase enzyme to produce DNA from its RNA genome, the reverse of the usual pattern, thus retro (backwards). This new DNA is then incorporated into the host cell genome by an integrase enzyme, at which point the retroviral DNA is referred to as a provirus. For example, the recombinant retroviruses such as the Moloney murine leukemia virus have the ability to integrate into the host genome in a stable fashion. They contain a reverse transcriptase that allows integration into the host genome. Retroviral vectors can either be replication-competent or replication-defective. In some embodiments of the invention, retroviruses are incorporated to effectuate transfection into a cell, however the CRISPR/Cas9/gRNA complexes are designed to target the viral genome.

In some embodiments of the invention, lentiviruses, which are a subclass of retroviruses, are used as viral vectors. Lentiviruses can be adapted as delivery vehicles (vectors) given their ability to integrate into the genome of non-dividing cells, which is the unique feature of lentiviruses as other retroviruses can infect only dividing cells. The viral genome in the form of RNA is reverse-transcribed when the virus enters the cell to produce DNA, which is then inserted into the genome at a random position by the viral integrase enzyme. The vector, now called a provirus, remains in the genome and is passed on to the progeny of the cell when it divides.

As opposed to lentiviruses, adenoviral DNA does not integrate into the genome and is not replicated during cell division. Adenovirus and the related AAV would be potential approaches as delivery vectors since they do not integrate into the host's genome. In some aspects of the invention, only the viral genome to be targeted is effected by the CRISPR/Cas9/gRNA complexes, and not the host's cells. Adeno-associated virus (AAV) is a small virus that infects humans and some other primate species. AAV can infect both dividing and non-dividing cells and may incorporate its genome into that of the host cell. For example, because of its potential use as a gene therapy vector, researchers have created an altered AAV called self-complementary adeno-associated virus (scAAV). Whereas AAV packages a single strand of DNA and requires the process of second-strand synthesis, scAAV packages both strands which anneal together to form double stranded DNA. By skipping second strand synthesis scAAV allows for rapid expression in the cell. Otherwise, scAAV carries many characteristics of its AAV counterpart. Methods of the invention may incorporate herpesvirus, poxvirus, alphavirus, or vaccinia virus as a means of delivery vectors.

In certain embodiments of the invention, non-viral vectors may be used to effectuate transfection. Methods of non-viral delivery of nucleic acids include lipofection, nucleofection, microinjection, biolistics, virosomes, liposomes, micelles, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam and Lipofectin). Cationic and neutral lipids that are suitable for efficient receptor-recognition lipofection of polynucleotides include those described in U.S. Pat. No. 7,166,298 to Jessee or U.S. Pat. No. 6,890,554 to Jesse, the contents of each of which are incorporated by reference. Delivery can be to cells (e.g. in vitro or ex vivo administration) or target tissues (e.g. in vivo administration).

Synthetic vectors are typically based on cationic lipids or polymers which can complex with negatively charged nucleic acids to form particles with a diameter in the order of 100 nm. The complex protects nucleic acid from degradation by nuclease. Moreover, cellular and local delivery strategies have to deal with the need for internalization, release, and distribution in the proper subcellular compartment. Systemic delivery strategies encounter additional hurdles, for example, strong interaction of cationic delivery vehicles with blood components, uptake by the reticuloendothelial system, kidney filtration, toxicity and targeting ability of the carriers to the cells of interest. Modifying the surfaces of the cationic non-virals can minimize their interaction with blood components, reduce reticuloendothelial system uptake, decrease their toxicity and increase their binding affinity with the target cells. Binding of plasma proteins (also termed opsonization) is the primary mechanism for RES to recognize the circulating nanoparticles. For example, macrophages, such as the Kupffer cells in the liver, recognize the opsonized nanoparticles via the scavenger receptor.

In some embodiments of the invention, non-viral vectors are modified to effectuate targeted delivery and transfection. PEGylation (i.e. modifying the surface with polyethyleneglycol) is the predominant method used to reduce the opsonization and aggregation of non-viral vectors and minimize the clearance by reticuloendothelial system, leading to a prolonged circulation lifetime after intravenous (i.v.) administration. PEGylated nanoparticles are therefore often referred as "stealth" nanoparticles. The nanoparticles that are not rapidly cleared from the circulation will have a chance to encounter infected cells.

However, PEG on the surface can decrease the uptake by target cells and reduce the biological activity. Therefore, to attach targeting ligand to the distal end of the PEGylated component is necessary; the ligand is projected beyond the PEG "shield" to allow binding to receptors on the target cell surface. When cationic liposome is used as gene carrier, the application of neutral helper lipid is helpful for the release of nucleic acid, besides promoting hexagonal phase formation to enable endosomal escape. In some embodiments of the invention, neutral or anionic liposomes are developed for systemic delivery of nucleic acids and obtaining therapeutic effect in experimental animal model. Designing and synthesizing novel cationic lipids and polymers, and covalently or noncovalently binding gene with peptides, targeting ligands, polymers, or environmentally sensitive moieties also attract many attentions for resolving the problems encountered by non-viral vectors. The application of inorganic nanoparticles (for example, metallic nanoparticles, iron oxide, calcium phosphate, magnesium phosphate, manganese phosphate, double hydroxides, carbon nanotubes, and quantum dots) in delivery vectors can be prepared and surface-functionalized in many different ways.

In some embodiments of the invention, targeted controlled-release systems responding to the unique environments of tissues and external stimuli are utilized. Gold nanorods have strong absorption bands in the near-infrared region, and the absorbed light energy is then converted into heat by gold nanorods, the so-called 'photothermal effect'. Because the near-infrared light can penetrate deeply into tissues, the surface of gold nanorod could be modified with nucleic acids for controlled release. When the modified gold nanorods are irradiated by near-infrared light, nucleic acids are released due to thermo-denaturation induced by the photothermal effect. The amount of nucleic acids released is dependent upon the power and exposure time of light irradiation.

In some embodiments of the invention, liposomes are used to effectuate transfection into a cell or tissue. A "liposome" as used herein refers to a small, spherical vesicle composed of lipids, particularly vesicle-forming lipids capable of spontaneously arranging into lipid bilayer structures in water with its hydrophobic moiety in contact with the interior, hydrophobic region of the bilayer membrane, and its head group moiety oriented toward the exterior, polar surface of the membrane. Vesicle-forming lipids have typically two hydrocarbon chains, particularly acyl chains, and a head group, either polar or nonpolar. Vesicle-forming lipids are either composed of naturally-occurring lipids or of synthetic origin, including the phospholipids, such as phosphatidylcholine, phosphatidylethanolamine, phosphatidic acid, phosphatidylinositol, and sphingomyelin, where the two hydrocarbon chains are typically between about 14-22 carbon atoms in length, and have varying degrees of unsaturation. The above-described lipids and phospholipids whose acyl chains have varying degrees of saturation can be obtained commercially or prepared according to published methods. Other suitable lipids for use in the composition of the present invention include glycolipids and sterols such as cholesterol and its various analogs which can also be used in the liposomes.

Similar to a liposome, a micelle is a small spherical vesicle composed of lipids, but is arranged as a lipid monolayer, with the hydrophilic head regions of the lipid molecules in contact with surrounding solvent, sequestering the hydrophobic single-tail regions in the center of the micelle. This phase is caused by the packing behavior of single-tail lipids in a bilayer.

The pharmacology of a liposomal formulation of nucleic acid is largely determined by the extent to which the nucleic acid is encapsulated inside the liposome bilayer. Encapsulated nucleic acid is protected from nuclease degradation, while those merely associated with the surface of the liposome is not protected. Encapsulated nucleic acid shares the extended circulation lifetime and biodistribution of the intact liposome, while those that are surface associated adopt the pharmacology of naked nucleic acid once they disassociate from the liposome.

In some embodiments, the complexes of the invention are encapsulated in a liposome. Unlike small molecule drugs, nucleic acids cannot cross intact lipid bilayers, predominantly due to the large size and hydrophilic nature of the nucleic acid. Therefore, nucleic acids may be entrapped within liposomes with conventional passive loading technologies, such as ethanol drop method (as in SALP), reverse-phase evaporation method, and ethanol dilution method (as in SNALP).

In some embodiments, linear polyethylenimine (L-PEI) is used as a non-viral vector due to its versatility and comparatively high transfection efficiency. L-PEI has been used to efficiently deliver genes in vivo into a wide range of organs such as lung, brain, pancreas, retina, bladder as well as tumor. L-PEI is able to efficiently condense, stabilize and deliver nucleic acids in vitro and in vivo.

Low-intensity ultrasound in combination with microbubbles has recently acquired much attention as a safe method of gene delivery. Ultrasound shows tissue-permeabilizing effect. It is non-invasive and site-specific, and could make it possible to destroy tumor cells after systemic delivery, while leave nontargeted organs unaffected. Ultrasound-mediated microbubbles destruction has been proposed as an innovative method for noninvasive delivering of drugs and nucleic acids to different tissues. Microbubbles are used to carry a drug or gene until a specific area of interest is reached, and then ultrasound is used to burst the microbubbles, causing site-specific delivery of the bioactive materials. Furthermore, the ability of albumin-coated microbubbles to adhere to vascular regions with glycocalix damage or endothelial dysfunction is another possible mechanism to deliver drugs even in the absence of ultrasound. See Tsutsui et al., 2004, The use of microbubbles to target drug delivery, Cardiovasc Ultrasound 2:23, the contents of which are incorporated by reference. In ultrasound-triggered drug delivery, tissue-permeabilizing effect can be potentiated using ultrasound contrast agents, gas-filled microbubbles. The use of microbubbles for delivery of nucleic acids is based on the hypothesis that destruction of DNA-loaded microbubbles by a focused ultrasound beam during their microvascular transit through the target area will result in localized transduction upon disruption of the microbubble shell while sparing non-targeted areas.

Besides ultrasound-mediated delivery, magnetic targeting delivery could be used for delivery. Magnetic nanoparticles are usually entrapped in gene vectors for imaging the delivery of nucleic acid. Nucleic acid carriers can be responsive to both ultrasound and magnetic fields, i.e., magnetic and acoustically active liposheres (MAALs). The basic premise is that therapeutic agents are attached to, or encapsulated within, a magnetic micro- or nanoparticle. These particles may have magnetic cores with a polymer or metal coating which can be functionalized, or may consist of porous polymers that contain magnetic nanoparticles precipitated within the pores. By functionalizing the polymer or metal coating it is possible to attach, for example, cytotoxic drugs for targeted chemotherapy or therapeutic DNA to correct a genetic defect. Once attached, the particle/therapeutic agent complex is injected into the bloodstream, often using a catheter to position the injection site near the target. Magnetic fields, generally from high-field, high-gradient, rare earth magnets are focused over the target site and the forces on the particles as they enter the field allow them to be captured and extravasated at the target.

Synthetic cationic polymer-based nanoparticles (~100 nm diameter) have been developed that offer enhanced transfection efficiency combined with reduced cytotoxicity, as compared to traditional liposomes. The incorporation of distinct layers composed of lipid molecules with varying physical and chemical characteristics into the polymer nanoparticle formulation resulted in improved efficiency through better fusion with cell membrane and entry into the cell, enhanced release of molecules inside the cell, and reduced intracellular degradation of nanoparticle complexes.

In some embodiments, the complexes are conjugated to nano-systems for systemic therapy, such as liposomes, albumin-based particles, PEGylated proteins, biodegradable polymer-drug composites, polymeric micelles, dendrimers, among others. See Davis et al., 2008, Nanotherapeutic particles: an emerging treatment modality for cancer, Nat Rev Drug Discov. 7(9):771-782, incorporated by reference. Long circulating macromolecular carriers such as liposomes, can exploit the enhanced permeability and retention effect for preferential extravasation from tumor vessels. In certain embodiments, the complexes of the invention are conjugated to or encapsulated into a liposome or polymerosome for delivery to a cell. For example, liposomal anthracyclines have achieved highly efficient encapsulation, and include versions with greatly prolonged circulation such as liposomal daunorubicin and pegylated liposomal doxorubicin. See Krishna et al., Carboxymethylcellulose-sodium based transdermal drug delivery system for propranolol, J Pharm Pharmacol. 1996 April; 48(4):367-70.

Liposomal delivery systems provide stable formulation, provide improved pharmacokinetics, and a degree of 'passive' or 'physiological' targeting to tissues. Encapsulation of hydrophilic and hydrophobic materials, such as potential chemotherapy agents, are known. See for example U.S. Pat. No. 5,466,468 to Schneider, which discloses parenterally administrable liposome formulation comprising synthetic lipids; U.S. Pat. No. 5,580,571, to Hostetler et al. which discloses nucleoside analogues conjugated to phospholipids; U.S. Pat. No. 5,626,869 to Nyqvist, which discloses pharmaceutical compositions wherein the pharmaceutically active compound is heparin or a fragment thereof contained in a defined lipid system comprising at least one amphipatic and polar lipid component and at least one nonpolar lipid component.

Liposomes and polymerosomes can contain a plurality of solutions and compounds. In certain embodiments, the complexes of the invention are coupled to or encapsulated in polymersomes. As a class of artificial vesicles, polymersomes are tiny hollow spheres that enclose a solution, made using amphiphilic synthetic block copolymers to form the vesicle membrane. Common polymersomes contain an aqueous solution in their core and are useful for encapsulating and protecting sensitive molecules, such as drugs, enzymes, other proteins and peptides, and DNA and RNA fragments. The polymersome membrane provides a physical barrier that isolates the encapsulated material from external materials, such as those found in biological systems. Polymerosomes can be generated from double emulsions by known techniques, see Lorenceau et al., 2005, Generation of Polymerosomes from Double-Emulsions, Langmuir 21(20): 9183-6, incorporated by reference.

Some embodiments of the invention provide for a gene gun or a biolistic particle delivery system. A gene gun is a device for injecting cells with genetic information, where the payload may be an elemental particle of a heavy metal coated with plasmid DNA. This technique may also be referred to as bioballistics or biolistics. Gene guns have also been used to deliver DNA vaccines. The gene gun is able to transfect cells with a wide variety of organic and non-organic species, such as DNA plasmids, fluorescent proteins, dyes, etc.

Aspects of the invention provide for numerous uses of delivery vectors. Selection of the delivery vector is based upon the cell or tissue targeted and the specific makeup of the CRISPR/Cas9/gRNA. For example, in the EBV example discussed above, since lymphocytes are known for being resistant to lipofection, nucleofection (a combination of electrical parameters generated by a device called Nucleofector, with cell-type specific reagents to transfer a substrate directly into the cell nucleus and the cytoplasm) was necessitated for DNA delivery into the Raji cells. The Lonza pmax promoter drives Cas9 expression as it offered strong expression within Raji cells. 24 hours after nucleofection, obvious EGFP signals were observed from a small proportion of cells through fluorescent microscopy. The EGFP-positive cell population decreased dramatically, however, <10% transfection efficiency 48 hours after nucleofection was measured (FIG. 1B). A CRISPR plasmid that included the EBV origin of replication sequence, oriP yielded a transfection efficiency >60% (FIG. 1B).

Aspects of the invention utilize the CRISPR/Cas9/gRNA complexes for the targeted delivery. Common known pathways include transdermal, transmucal, nasal, ocular and pulmonary routes. Drug delivery systems may include liposomes, proliposomes, microspheres, gels, prodrugs, cyclodextrins, etc. Aspects of the invention utilize nanoparticles composed of biodegradable polymers to be transferred into an aerosol for targeting of specific sites or cell populations in the lung, providing for the release of the drug in a predetermined manner and degradation within an acceptable period of time. Controlled-release technology (CRT), such as transdermal and transmucosal controlled-release delivery systems, nasal and buccal aerosol sprays, drug-impregnated lozenges, encapsulated cells, oral soft gels, iontophoretic devices to administer drugs through skin, and a variety of programmable, implanted drug-delivery devices are used in conjunction with the complexes of the invention of accomplishing targeted and controlled delivery.

v. Digest Nucleic Acid

Once inside the cell, the CRISPR/Cas9/gRNA complexes target nucleic acid. In an aspect of the invention, the complexes are targeted to viral genomes. In addition to latent infections this invention can also be used to control actively replicating viruses by targeting the viral genome before it is packaged or after it is ejected. In some embodiments, methods and compositions of the invention use a nuclease such as Cas9 to target latent viral genomes, thereby reducing the chances of proliferation. The nuclease may form a complex with a gRNA (e.g., crRNA+tracrRNA or sgRNA). The complex cuts the viral nucleic acid in a targeted fashion to incapacitate the viral genome. As discussed above, the Cas9 endonuclease causes a double strand break in the viral genome. By targeted several locations along the viral genome and causing not a single strand break, but a double strand break, the genome is effectively cut a several locations along the genome. In a preferred embodiment, the double strand breaks are designed so that small deletions are caused, or small fragments are removed from the genome so that even if natural repair mechanisms join the genome together, the genome is render incapacitated.

After introduction into a cell, the CRISPR/Cas9/gRNA complexes act on the viral genome, genes, transcripts, or other viral nucleic acid. The double-strand DNA breaks generated by CRISPR are repaired with small deletions. These deletions will disrupt the protein coding and hence create knockout effects.

The nuclease, or a gene encoding the nuclease, may be delivered into an infected cell by transfection. For example, the infected cell can be transfected with DNA that encodes Cas9 and gRNA (on a single piece or separate pieces). The gRNAs are designed to localize the Cas9 endonuclease at one or several locations along the viral genome. The Cas9 endonuclease causes double strand breaks in the genome, causing small fragments to be deleted from the viral genome. Even with repair mechanisms, the deletions render the viral genome incapacitated.

Engineered viral particles with higher cell affinity (e.g. RGD knob) and specificity could greatly improve delivery efficiency. Delivery of circular instead of linear DNA may also be beneficial since the circular DNA can replicate as episomes with replication origins.

Aspects of the invention utilize the CRISPR/Cas9/gRNA complexes for the targeted delivery. Common known pathways include transdermal, transmucal, nasal, ocular and pulmonary routes. Drug delivery systems may include liposomes, proliposomes, micelles, microspheres, gels, prodrugs, cyclodextrins, etc. Aspects of the invention utilize nanoparticles composed of biodegradable polymers to be transferred into an aerosol for targeting of specific sites or cell populations in the lung, providing for the release of the drug in a predetermined manner and degradation within an acceptable period of time. Controlled-release technology (CRT), such as transdermal and transmucosal controlled-release delivery systems, nasal and buccal aerosol sprays, drug-impregnated lozenges, encapsulated cells, oral soft gels, iontophoretic devices to administer drugs through skin, and a variety of programmable, implanted drug-delivery devices are used in conjunction with the complexes of the invention of accomplishing targeted and controlled delivery.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1: Targeting EBV

Burkitt's lymphoma cell lines Raji, Namalwa, and DG-75 were obtained from ATCC and cultured in RPMI 1640 supplemented with 10% FBS and PSA, following ATCC recommendation. Human primary lung fibroblast IMR-90 was obtained from Coriell and cultured in Advanced DMEM/F-12 supplemented with 10% FBS and PSA.

Plasmids consisting of a U6 promoter driven chimeric guide RNA (sgRNA) and a ubiquitous promoter driven Cas9 were obtained from addgene, as described by Cong L et al. (2013) Multiplex Genome Engineering Using CRISPR/Cas Systems. Science 339:819-823. An EGFP marker fused after the Cas9 protein allowed selection of Cas9-positive cells (FIG. 1A). We adapted a modified chimeric guide RNA design for more efficient Pol-III transcription and more stable stem-loop structure (Chen B et al. (2013) Dynamic Imaging of Genomic Loci in Living Human Cells by an Optimized CRISPR/Cas System. Cell 155:1479-1491).

We obtained pX458 from Addgene, Inc. A modified CMV promoter with a synthetic intron (pmax) was PCR amplified from Lonza control plasmid pmax-GFP. A modified guide RNA sgRNA (F+E) was ordered from IDT. EBV replication origin oriP was PCR amplified from B95-8 transformed lymphoblastoid cell line GM12891. We used standard cloning protocols to clone pmax, sgRNA(F+E) and oriP to pX458, to replace the original CAG promoter, sgRNA and f1 origin. We designed EBV sgRNA based on the B95-8 reference, and ordered DNA oligos from IDT. The original sgRNA place holder in pX458 serves as the negative control.

Lymphocytes are known for being resistant to lipofection, and therefore we used nucleofection for DNA delivery into Raji cells. We chose the Lonza pmax promoter to drive Cas9 expression as it offered strong expression within Raji cells. We used the Lonza Nucleofector II for DNA delivery. 5 million Raji or DG-75 cells were transfected with 5 ug plasmids in each 100-ul reaction. Cell line Kit V and program M-013 were used following Lonza recommendation. For IMR-90, 1 million cells were transfected with 5 ug plasmids in 100 ul Solution V, with program T-030 or X-005. 24 hours after nucleofection, we observed obvious EGFP signals from a small proportion of cells through fluorescent microscopy. The EGFP-positive cell population decreased dramatically after that, however, and we measured <10% transfection efficiency 48 hours after nucleofection (FIG. 1B). We attributed this transfection efficiency decrease to the plasmid dilution with cell division. To actively maintain the plasmid level within the host cells, we redesigned the CRISPR plasmid to include the EBV origin of replication sequence, oriP. With active plasmid replication inside the cells, the transfection efficiency rose to >60% (FIG. 1B).

To design guide RNA targeting the EBV genome, we relied on the EBV reference genome from strain B95-8. We targeted six regions with seven guide RNA designs for different genome editing purposes (FIG. 1C and Table S1). EBNA1 is crucial for many EBV functions including gene regulation and latent genome replication. We targeted guide RNA sgEBV4 and sgEBV5 to both ends of the EBNA1 coding region in order to excise this whole region of the genome. Guide RNAs sgEBV1, 2 and 6 fall in repeat regions, so that the success rate of at least one CRISPR cut is multiplied. These "structural" targets enable systematic digestion of the EBV genome into smaller pieces. EBNA3C and LMP1 are essential for host cell transformation, and we designed guide RNAs sgEBV3 and sgEBV7 to target the 5' exons of these two proteins respectively.

Figure 5:
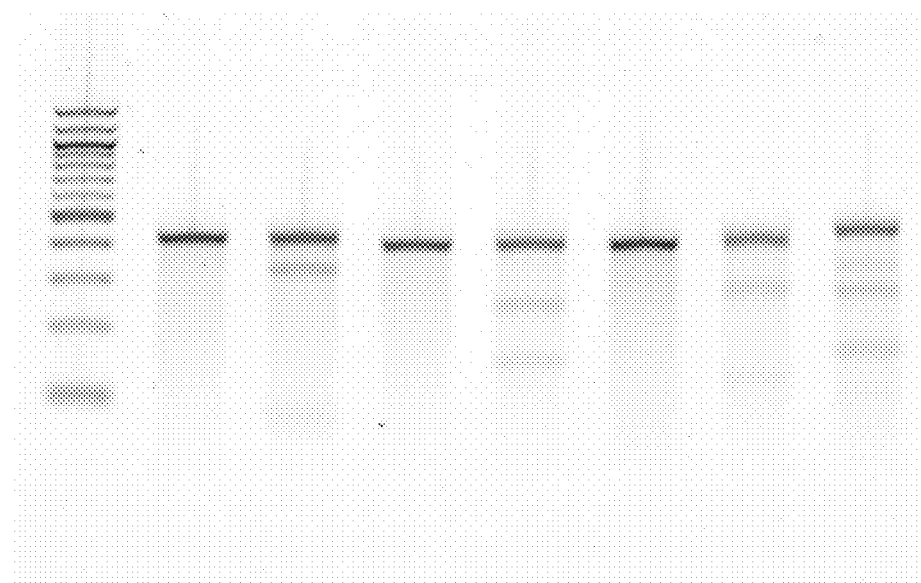
FIG. 5 represents SURVEYOR assay of EBV CRISPR. Lane 1: NEB 100 bp ladder; Lane 2: sgEBV1 control; Lane 3: sgEBV1; Lane 4: sgEBV5 control; Lane 5: sgEBV5; Lane 6: sgEBV7 control; Lane 7: sgEBV7; Lane 8: sgEBV4.

EBV Genome Editing. The double-strand DNA breaks generated by CRISPR are repaired with small deletions. These deletions will disrupt the protein coding and hence create knockout effects. SURVEYOR assays confirmed efficient editing of individual sites (FIG. 5). Beyond the independent small deletions induced by each guide RNA, large deletions between targeting sites can systematically destroy the EBV genome. Guide RNA sgEBV2 targets a region with twelve 125-bp repeat units (FIG. 2A). PCR amplicon of the whole repeat region gave a ~1.8-kb band (FIG. 2B). After 5 or 7 days of sgEBV2 transfection, we obtained ~0.4-kb bands from the same PCR amplification (FIG. 2B). The ~1.4-kb deletion is the expected product of repair ligation between cuts in the first and the last repeat unit (FIG. 2A).

DNA sequences flanking sgRNA targets were PCR amplified with Phusion DNA polymerase. SURVEYOR assays were performed following manufacturer's instruction. DNA amplicons with large deletions were TOPO cloned and single colonies were used for Sanger sequencing. EBV load was measured with Taqman digital PCR on Fluidigm Bio-Mark. A Taqman assay targeting a conserved human locus was used for human DNA normalization. 1 ng of single-cell whole-genome amplification products from Fluidigm C1 were used for EBV quantitative PCR.

Figure 2C:
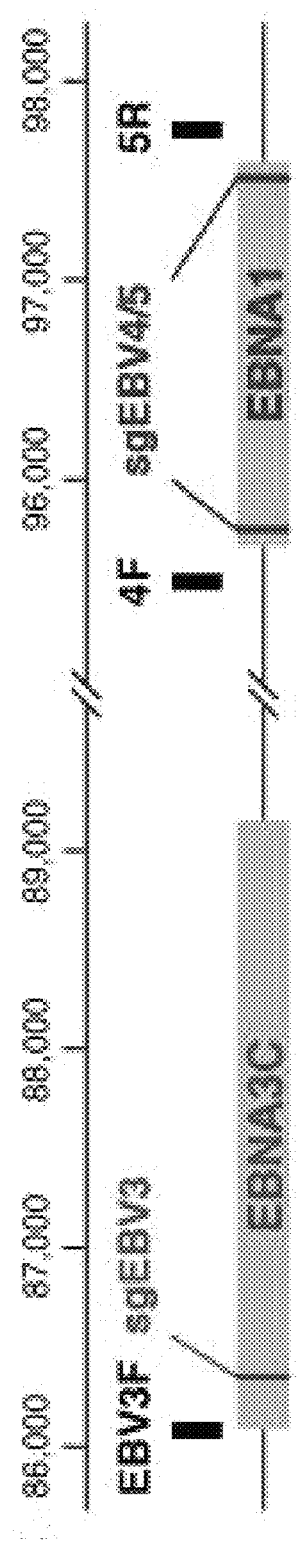
Figure 2D:
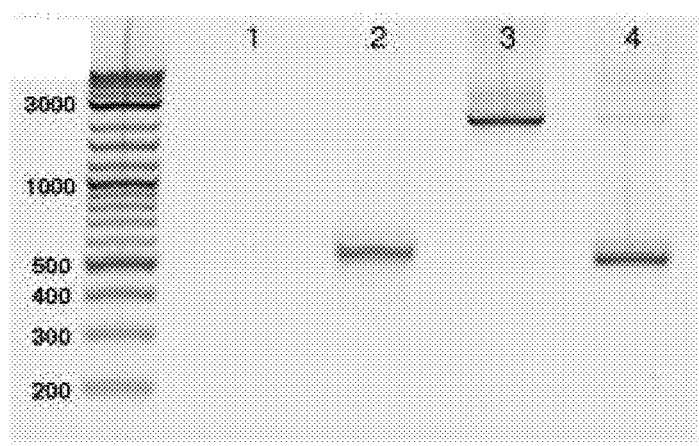
Figure 2E:
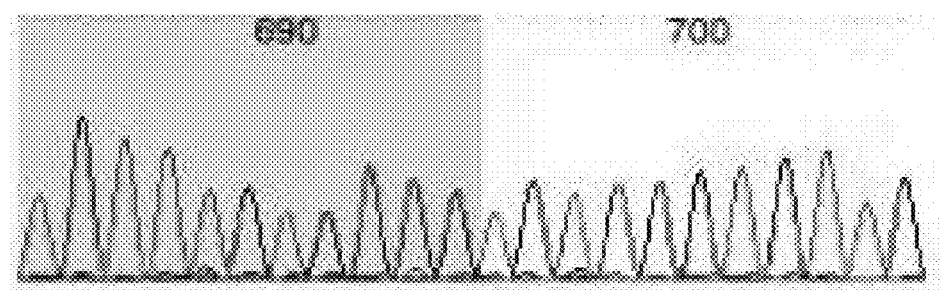
Figure 2F:
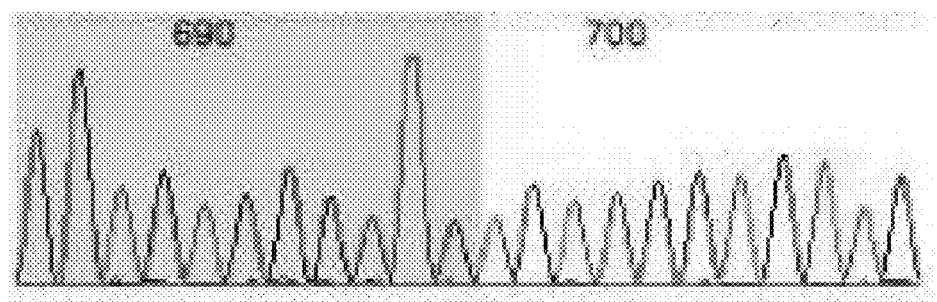
Figure 3A:
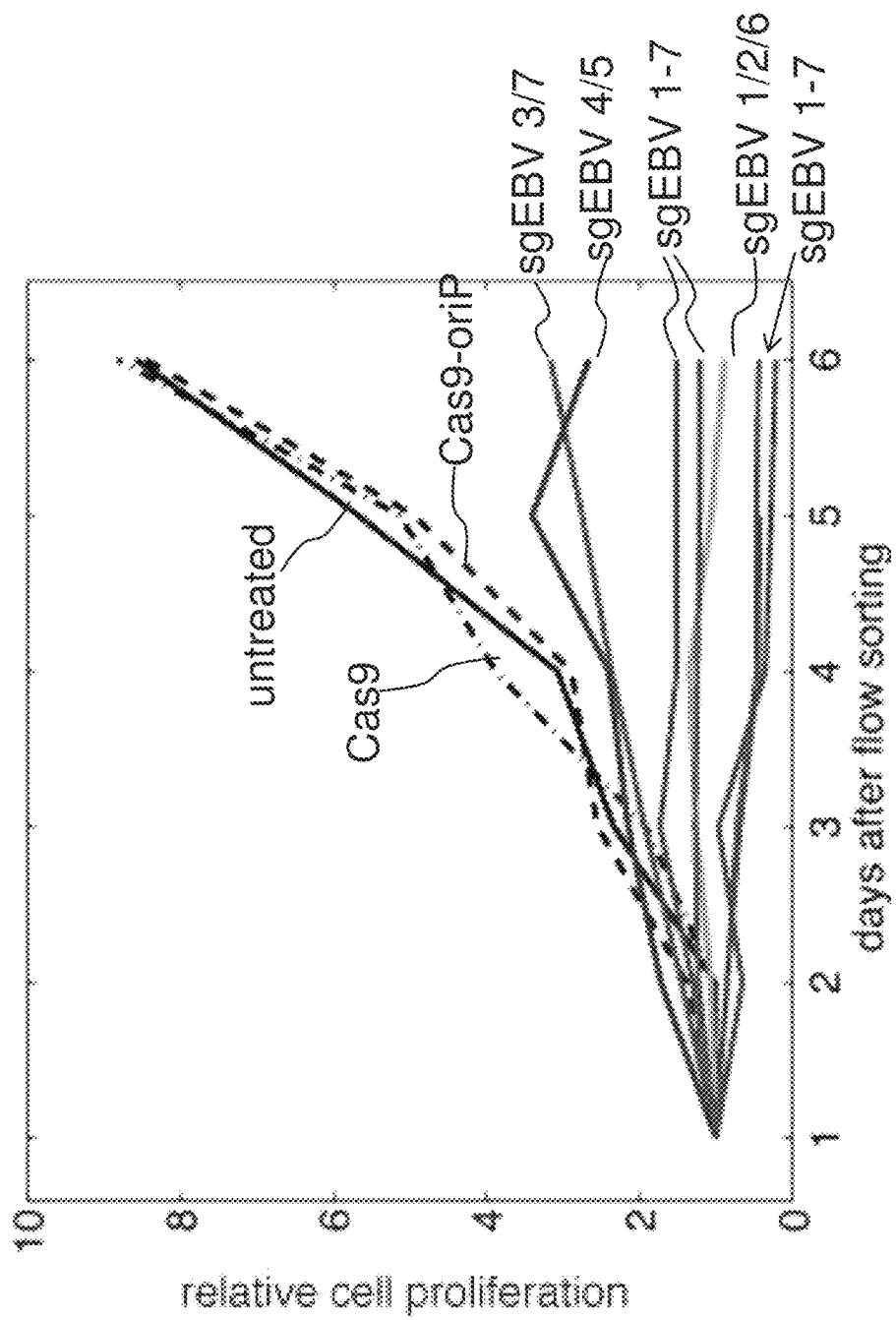
FIGS. 3A-3M represent cell proliferation arrest with EBV genome destruction.

We further demonstrated that it is possible to delete regions between unique targets (FIG. 2C). Six days after sgEBV4-5 transfection, PCR amplification of the whole flanking region (with primers EBV4F and 5R) returned a shorter amplicon, together with a much fainter band of the expected 2 kb (FIG. 2D). Sanger sequencing of amplicon clones confirmed the direct connection of the two expected cutting sites (FIG. 2F). A similar experiment with sgEBV3-5 also returned an even larger deletion, from EBNA3C to EBNA1 (FIG. 2D-E).

Figure 3B:
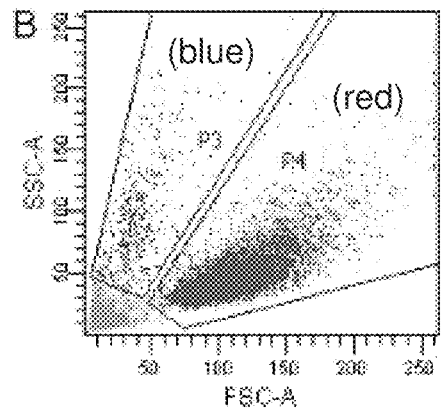
Figure 3E:
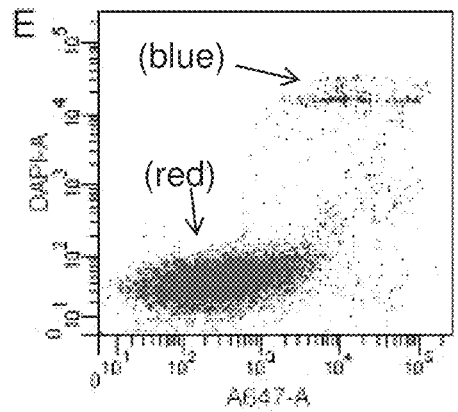
Figure 3C:
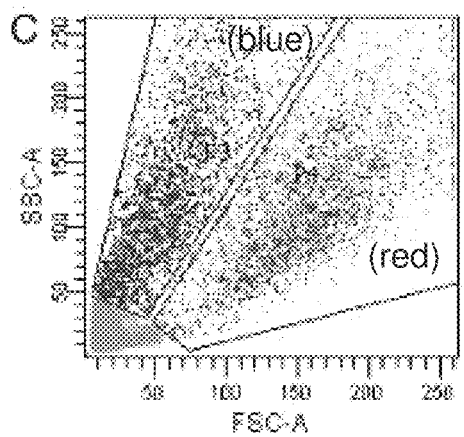
Figure 3F:
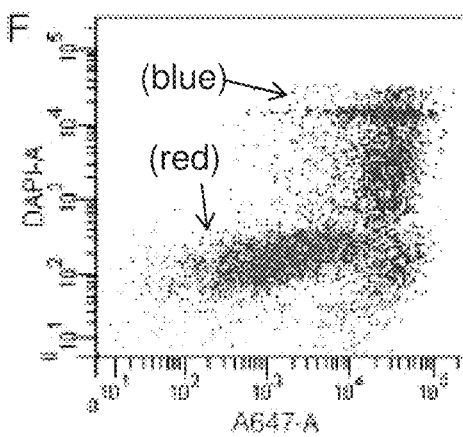
Figure 3D:
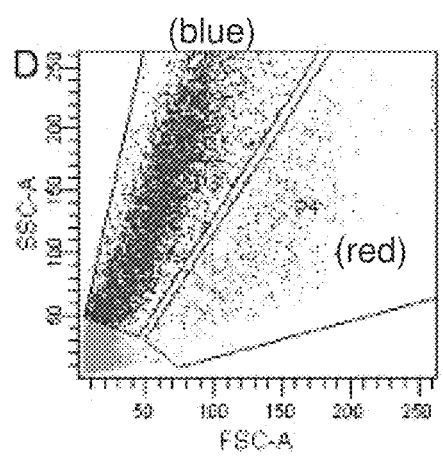
Figure 3G:
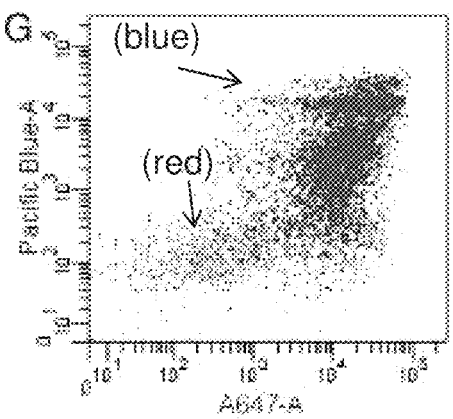
Figure 6:
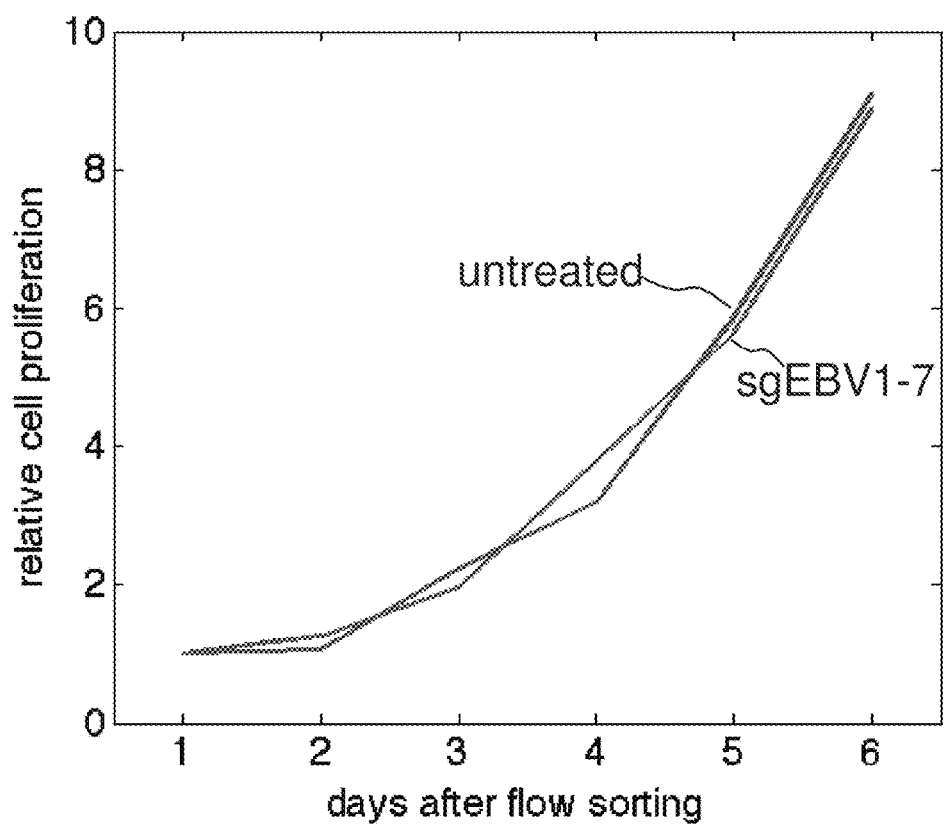
FIG. 6 shows CRISPR cytotoxicity test with EBV-negative Burkitt's lymphoma DG-75.
Figure 7:
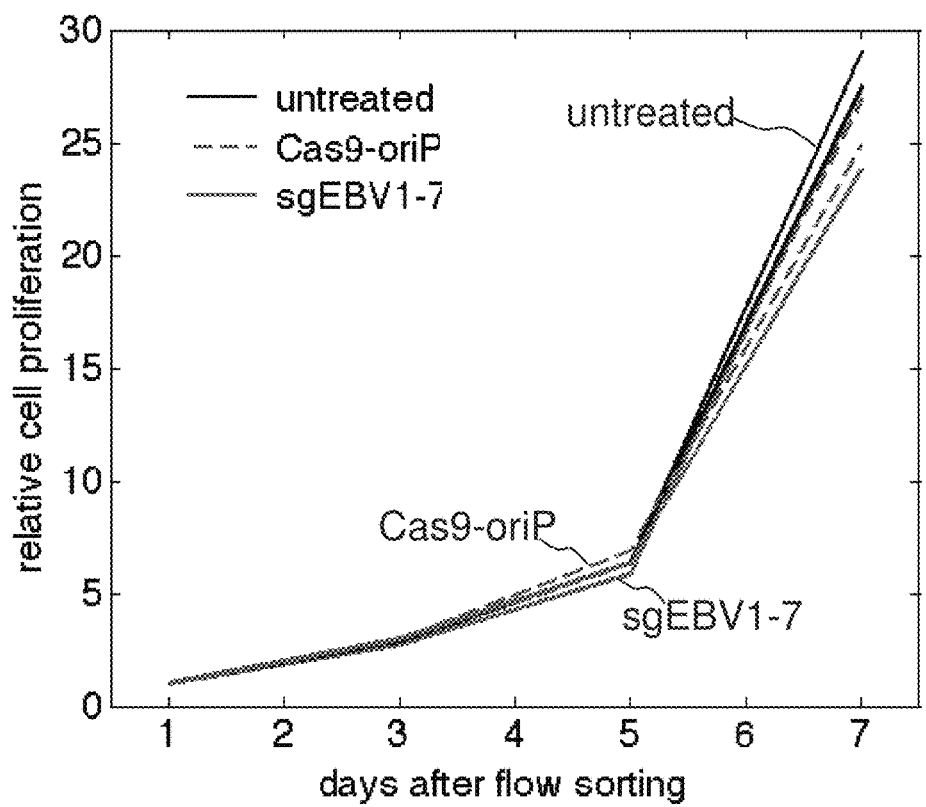
FIG. 7 represents CRISPR cytotoxicity test with primary human lung fibroblast IMR-90.

Cell Proliferation Arrest With EBV Genome Destruction. Two days after CRISPR transfection, we flow sorted EGFP-positive cells for further culture and counted the live cells daily. As expected, cells treated with Cas9 plasmids which lacked oriP or sgEBV lost EGFP expression within a few days and proliferated with a rate similar rate to the untreated control group (FIG. 3A). Plasmids with Cas9-oriP and a scrambled guide RNA maintained EGFP expression after 8 days, but did not reduce the cell proliferation rate. Treatment with the mixed cocktail sgEBV1-7 resulted in no measurable cell proliferation and the total cell count either remained constant or decreased (FIG. 3A). Flow cytometry scattering signals clearly revealed alterations in the cell morphology after sgEBV1-7 treatment, as the majority of the cells shrank in size with increasing granulation (FIG. 3B-D, population P4 to P3 shift). Cells in population P3 also demonstrated compromised membrane permeability by DAPI staining (FIG. 3E-G). To rule out the possibility of CRISPR cytotoxicity, especially with multiple guide RNAs, we performed the same treatment on two other samples: the EBV-negative Burkitt's lymphoma cell line DG-75 (FIG. 6) and primary human lung fibroblast IMR90 (FIG. 7). Eight and nine days after transfection the cell proliferation rates did not change from the untreated control groups, suggesting neglectable cytotoxicity.

Figure 3H:
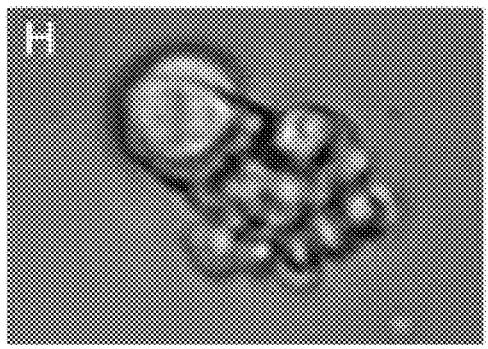
Figure 3I:
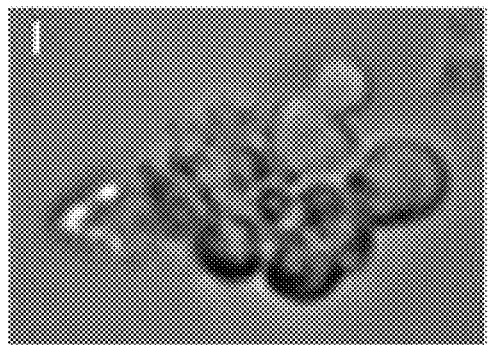
Figure 3J:
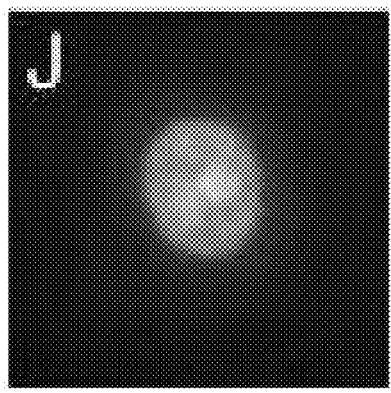
Figure 3K:
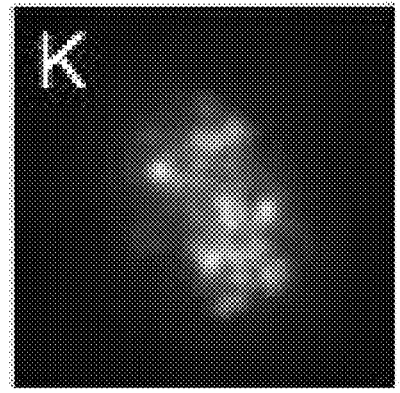
Figure 3L:
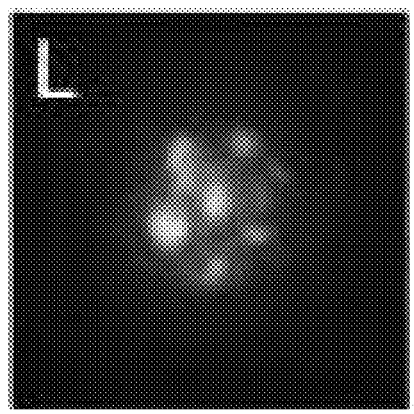
Figure 3M:
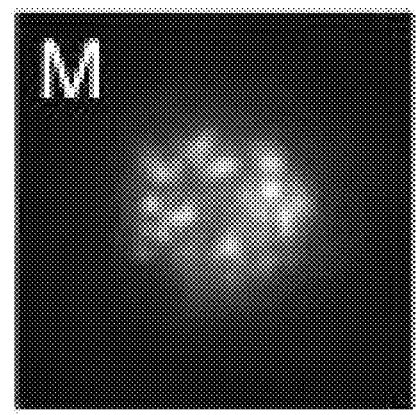

Previous studies have attributed the EBV tumorigenic ability to its interruption of host cell apoptosis (Ruf I K et al. (1999) Epstein-Barr Virus Regulates c-MYC, Apoptosis, and Tumorigenicity in Burkitt Lymphoma. Molecular and Cellular Biology 19:1651-1660). Suppressing EBV activities may therefore restore the apoptosis process, which could explain the cell death observed in our experiment Annexin V staining revealed a distinct subpopulation of cells with intact cell membrane but exposed phosphatidylserine, suggesting cell death through apoptosis (FIG. 3E-G). Bright field microscopy showed obvious apoptotic cell morphology (FIG. 3H-I) and fluorescent staining demonstrated drastic DNA fragmentation (FIG. 3J-M). Altogether this evidence suggests restoration of the normal host cell apoptosis pathway after EBV genome destruction.

Figure 4A:
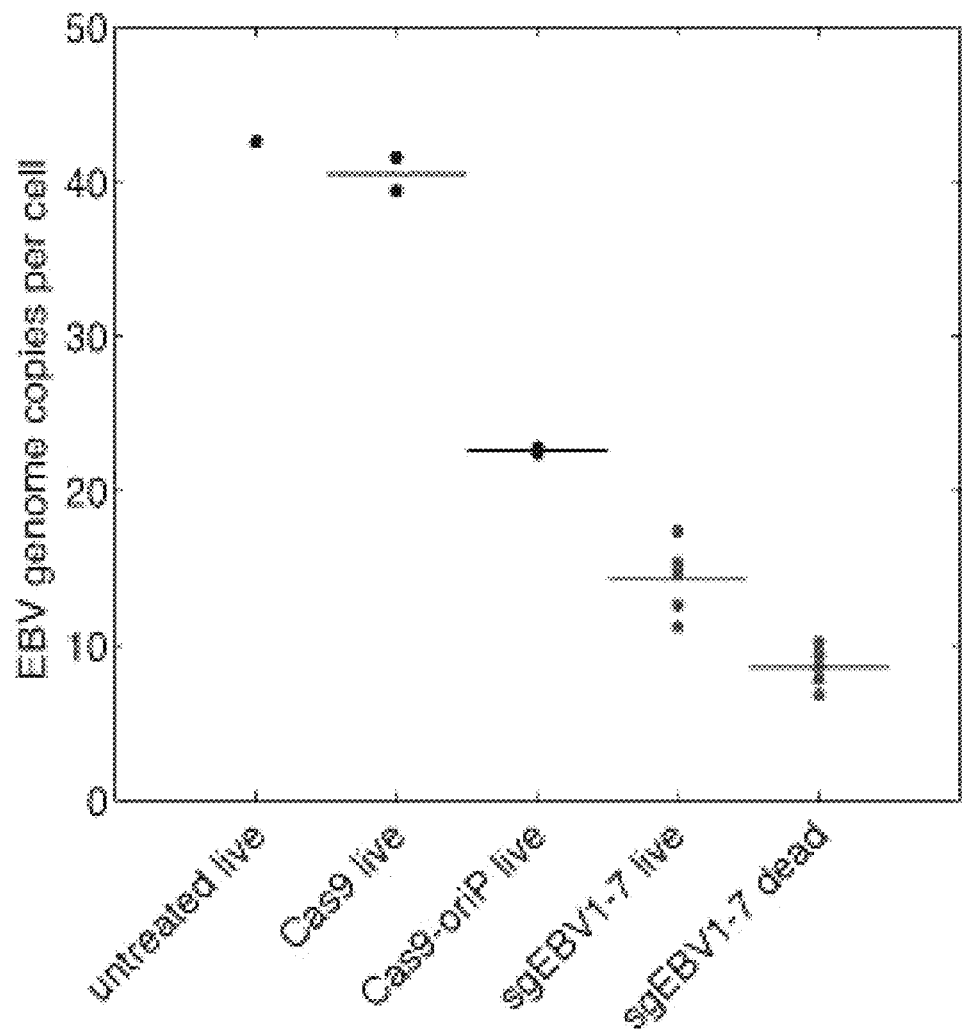
FIGS. 4A-4E represent EBV load quantitation after CRISPR treatment.

Complete Clearance Of EBV In A Subpopulation. To study the potential connection between cell proliferation arrest and EBV genome editing, we quantified the EBV load in different samples with digital PCR targeting EBNA1. Another Taqman assay targeting a conserved human somatic locus served as the internal control for human DNA normalization. On average, each untreated Raji cell has 42 copies of EBV genome (FIG. 4A). Cells treated with a Cas9 plasmid that lacked oriP or sgEBV did not have an obvious difference in EBV load difference from the untreated control. Cells treated with a Cas9-plasmid with oriP but no sgEBV had an EBV load that was reduced by ~50%. In conjunction with the prior observation that cells from this experiment did not show any difference in proliferation rate, we interpret this as likely due to competition for EBNA1 binding during plasmid replication. The addition of the guide RNA cocktail sgEBV1-7 to the transfection dramatically reduced the EBV load. Both the live and dead cells have >60% EBV decrease comparing to the untreated control.

Figure 4B:
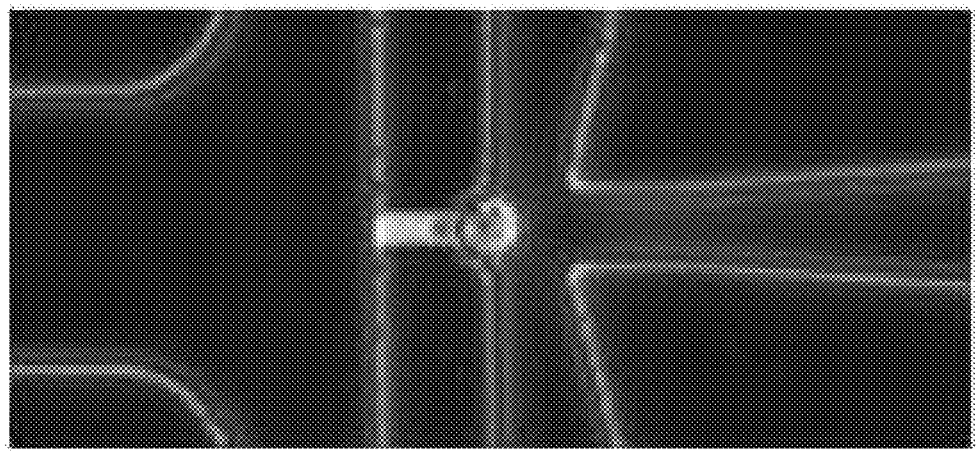
Figure 4C:
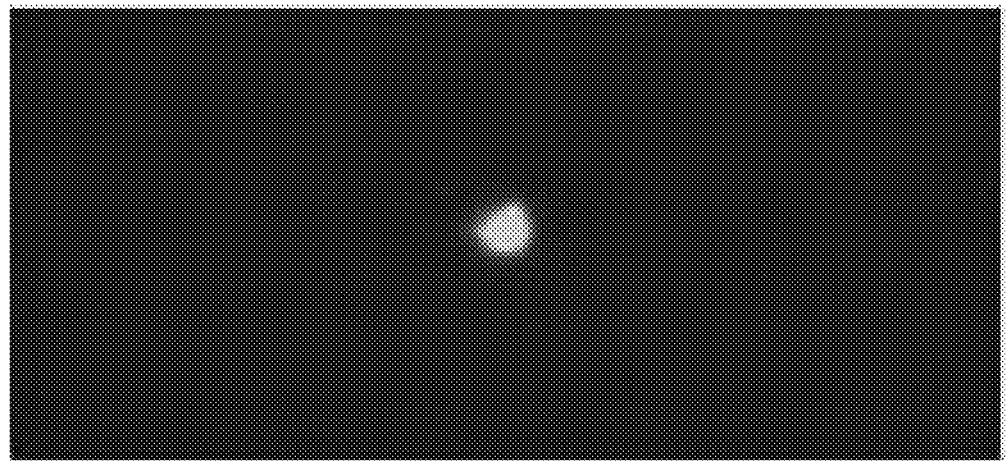
Figure 4D:
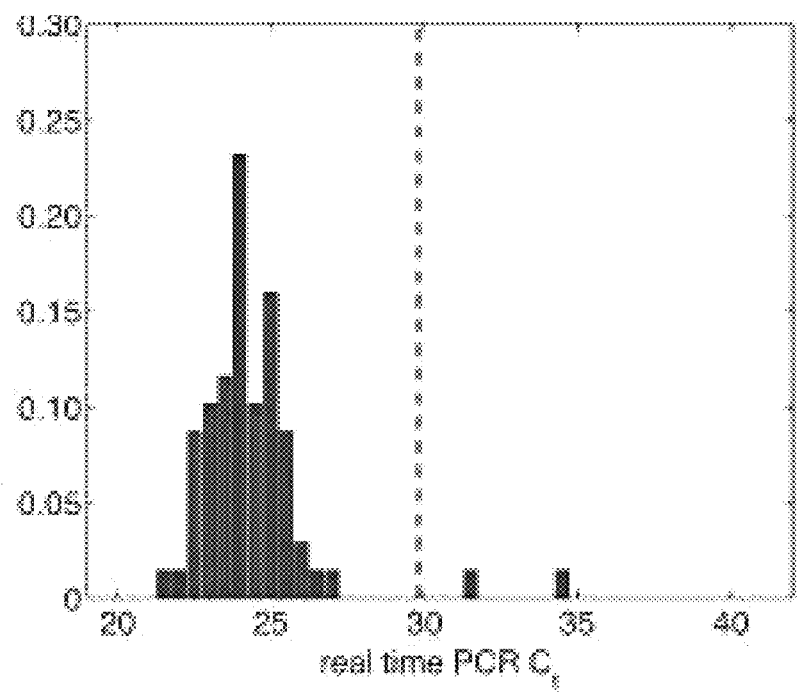
Figure 4E:
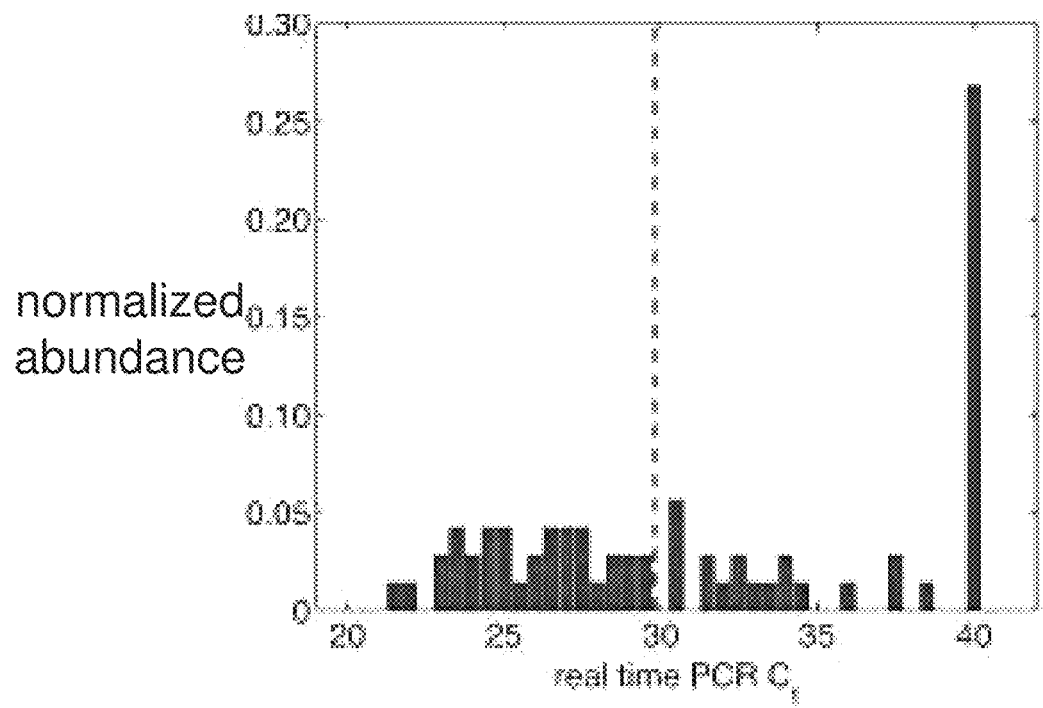

Although we provided seven guide RNAs at the same molar ratio, the plasmid transfection and replication process is likely quite stochastic. Some cells will inevitably receive different subsets or mixtures of the guide RNA cocktail, which might affect the treatment efficiency. To control for such effects, we measured EBV load at the single cell level by employing single-cell whole-genome amplification with an automated microfluidic system. We loaded freshly cultured Raji cells onto the microfluidic chip and captured 81 single cells (FIG. 4B). For the sgEBV1-7 treated cells, we flow sorted the live cells eight days after transfection and captured 91 single cells (FIG. 4C). Following manufacturer's instruction, we obtained ~150 ng amplified DNA from each single cell reaction chamber. For quality control purposes we performed 4-loci human somatic DNA quantitative PCR on each single cell amplification product (Wang J, Fan H C, Behr B, Quake S R (2012) Genome-wide single-cell analysis of recombination activity and de novo mutation rates in human sperm. Cell 150:402-412) and required positive amplification from at least one locus. 69 untreated single-cell products passed the quality control and displayed a log-normal distribution of EBV load (FIG. 4D) with almost every cell displaying significant amounts of EBV genomic DNA. We calibrated the quantitative PCR assay with a subclone of Namalwa Burkitt's lymphoma cells, which contain a single integrated EBV genome. The single-copy EBV measurements gave a Ct of 29.8, which enabled us to determine that the mean Ct of the 69 Raji single cell samples corresponded to 42 EBV copies per cells, in concordance with the bulk digital PCR measurement. For the sgEBV1-7 treated sample, 71 single-cell products passed the quality control and the EBV load distribution was dramatically wider (FIG. 4E). While 22 cells had the same EBV load as the untreated cells, 19 cells had no detectable EBV and the remaining 30 cells displayed dramatic EBV load decrease from the untreated sample.

Essential Targets For EBV Treatment. The seven guide RNAs in our CRISPR cocktail target three different categories of sequences which are important for EBV genome structure, host cell transformation, and infection latency, respectively. To understand the most essential targets for effective EBV treatment, we transfected Raji cells with subsets of guide RNAs. Although sgEBV4/5 reduced the EBV genome by 85%, they could not suppress cell proliferation as effectively as the full cocktail (FIG. 3A). Guide RNAs targeting the structural sequences (sgEBV1/2/6) could stop cell proliferation completely, despite not eliminating the full EBV load (26% decrease). Given the high efficiency of genome editing and the proliferation arrest (FIG. 2), we suspect that the residual EBV genome signature in sgEBV1/2/6 was not due to intact genomes but to free-floating DNA that has been digested out of the EBV genome, i.e. as a false positive. We conclude that systematic destruction of EBV genome structure appears to be more effective than targeting specific key proteins for EBV treatment.

Additional information such as primer design is shown in Wang and Quake, 2014, RNA-guided endonuclease provides a therapeutic strategy to cure latent herpesviridae infection, PNAS 111(36):13157-13162 and in the Supporting Information to that article published online at the PNAS website, and the contents of both of those documents are incorporated by reference for all purposes.

Example 2: Targeting Hepatitis B Virus (HBV)

Methods and materials of the present invention may be used to apply targeted endonuclease to specific genetic material such as a latent viral genome like the hepatitis B virus (HBV). The invention further provides for the efficient and safe delivery of nucleic acid (such as a DNA plasmid) into target cells (e.g., hepatocytes). In one embodiment, methods of the invention use hydrodynamic gene delivery to target HBV.

Figure 10:
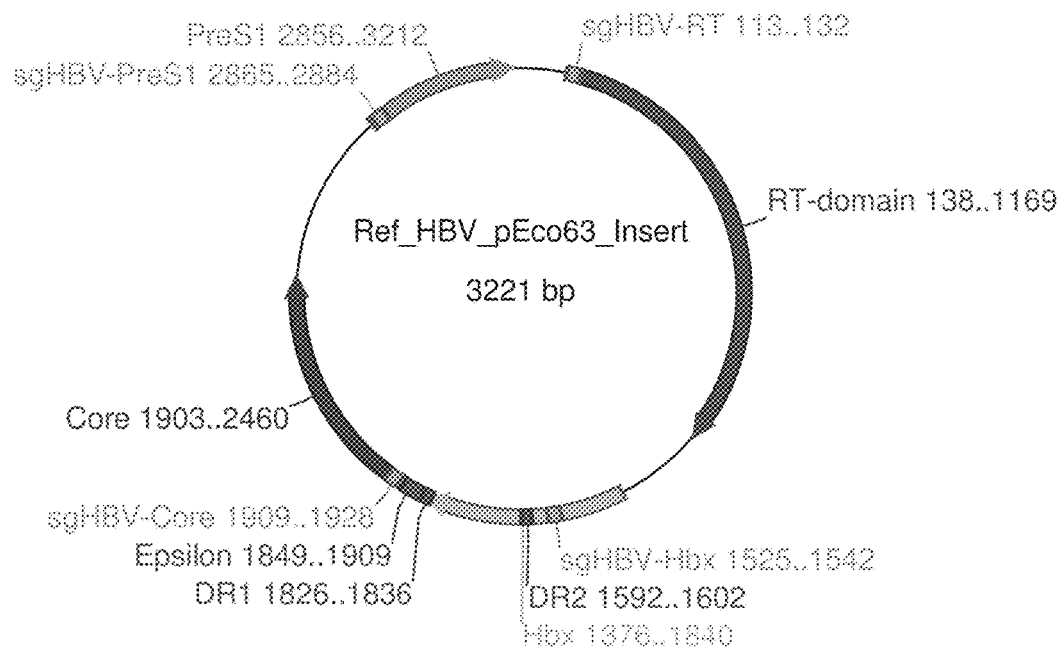
FIG. 10 is a map of an HBV genome.

FIG. 10 diagrams the HBV genome. It may be preferable to receive annotations for the HBV genome (i.e., that identify important features of the genome) and choose a candidate for targeting by enzymatic degradation that lies within one of those features, such as a viral replication origin, a terminal repeat, a replication factor binding site, a promoter, a coding sequence, and a repetitive region.

HBV, which is the prototype member of the family Hepadnaviridae, is a 42 nm partially double stranded DNA virus, composed of a 27 nm nucleocapsid core (HBcAg), surrounded by an outer lipoprotein coat (also called envelope) containing the surface antigen (HBsAg). The virus includes an enveloped virion containing 3 to 3.3 kb of relaxed circular, partially duplex DNA and virion-associated DNA-dependent polymerases that can repair the gap in the virion DNA template and has reverse transcriptase activities. HBV is a circular, partially double-stranded DNA virus of approximately 3200 bp with four overlapping ORFs encoding the polymerase (P), core (C), surface (S) and X proteins. In infection, viral nucleocapsids enter the cell and reach the nucleus, where the viral genome is delivered. In the nucleus, second-strand DNA synthesis is completed and the gaps in both strands are repaired to yield a covalently closed circular DNA molecule that serves as a template for transcription of four viral RNAs that are 3.5, 2.4, 2.1, and 0.7 kb long. These transcripts are polyadenylated and transported to the cytoplasm, where they are translated into the viral nucleocapsid and precore antigen (C, pre-C), polymerase (P), envelope L (large), M (medium), S (small)), and transcriptional trans-activating proteins (X). The envelope proteins insert themselves as integral membrane proteins into the lipid membrane of the endoplasmic reticulum (ER). The 3.5 kb species, spanning the entire genome and termed pregenomic RNA (pgRNA), is packaged together with HBV polymerase and a protein kinase into core particles where it serves as a template for reverse transcription of negative-strand DNA. The RNA to DNA conversion takes place inside the particles.

Numbering of basepairs on the HBV genome is based on the cleavage site for the restriction enzyme EcoR1 or at homologous sites, if the EcoR1 site is absent. However, other methods of numbering are also used, based on the start codon of the core protein or on the first base of the RNA pregenome. Every base pair in the HBV genome is involved in encoding at least one of the HBV protein. However, the genome also contains genetic elements which regulate levels of transcription, determine the site of polyadenylation, and even mark a specific transcript for encapsidation into the nucleocapsid. The four ORFs lead to the transcription and translation of seven different HBV proteins through use of varying in-frame start codons. For example, the small hepatitis B surface protein is generated when a ribosome begins translation at the ATG at position 155 of the adw genome. The middle hepatitis B surface protein is generated when a ribosome begins at an upstream ATG at position 3211, resulting in the addition of 55 amino acids onto the 5' end of the protein.

ORF P occupies the majority of the genome and encodes for the hepatitis B polymerase protein. ORF S encodes the three surface proteins. ORF C encodes both the hepatitis e and core protein. ORF X encodes the hepatitis B X protein. The HBV genome contains many important promoter and signal regions necessary for viral replication to occur. The four ORFs transcription are controlled by four promoter elements (preS1, preS2, core and X), and two enhancer elements (Enh I and Enh II). All HBV transcripts share a common adenylation signal located in the region spanning 1916-1921 in the genome. Resulting transcripts range from 3.5 nucleotides to 0.9 nucleotides in length. Due to the location of the core/pregenomic promoter, the polyadenylation site is differentially utilized. The polyadenylation site is a hexanucleotide sequence (TATAAA) as opposed to the canonical eukaryotic polyadenylation signal sequence (AATAAA). The TATAAA is known to work inefficiently (9), suitable for differential use by HBV.

There are four known genes encoded by the genome, called C, X, P, and S. The core protein is coded for by gene C (HBcAg), and its start codon is preceded by an upstream in-frame AUG start codon from which the pre-core protein is produced. HBeAg is produced by proteolytic processing of the pre-core protein. The DNA polymerase is encoded by gene P. Gene S is the gene that codes for the surface antigen (HBsAg). The HBsAg gene is one long open reading frame but contains three in-frame start (ATG) codons that divide the gene into three sections, pre-S1, pre-S2, and S. Because of the multiple start codons, polypeptides of three different sizes called large, middle, and small (pre-S1+pre-S2+S, pre-S2+S, or S) are produced. The function of the protein coded for by gene X is not fully understood but it is associated with the development of liver cancer. It stimulates genes that promote cell growth and inactivates growth regulating molecules.

With reference to FIG. 10, HBV starts its infection cycle by binding to the host cells with PreS1. Guide RNA against PreS1 locates at the 5' end of the coding sequence. Endonuclease digestion will introduce insertion/deletion, which leads to frame shift of PreS1 translation. HBV replicates its genome through the form of long RNA, with identical repeats DR1 and DR2 at both ends, and RNA encapsidation signal epsilon at the 5' end. The reverse transcriptase domain (RT) of the polymerase gene converts the RNA into DNA. Hbx protein is a key regulator of viral replication, as well as host cell functions. Digestion guided by RNA against RT will introduce insertion/deletion, which leads to frame shift of RT translation. Guide RNAs sgHbx and sgCore can not only lead to frame shift in the coding of Hbx and HBV core protein, but also deletion the whole region containing DR2-DR1-Epsilon. The four sgRNA in combination can also lead to systemic destruction of HBV genome into small pieces.

HBV replicates its genome by reverse transcription of an RNA intermediate. The RNA templates is first converted into single-stranded DNA species (minus-strand DNA), which is subsequently used as templates for plus-strand DNA synthesis. DNA synthesis in HBV use RNA primers for plus-strand DNA synthesis, which predominantly initiate at internal locations on the single-stranded DNA. The primer is generated via an RNase H cleavage that is a sequence independent measurement from the 5' end of the RNA template. This 18 nt RNA primer is annealed to the 3' end of the minus-strand DNA with the 3' end of the primer located within the 12 nt direct repeat, DR1. The majority of plus-strand DNA synthesis initiates from the 12 nt direct repeat, DR2, located near the other end of the minus-strand DNA as a result of primer translocation. The site of plus-strand priming has consequences. In situ priming results in a duplex linear (DL) DNA genome, whereas priming from DR2 can lead to the synthesis of a relaxed circular (RC) DNA genome following completion of a second template switch termed circularization. It remains unclear why hepadnaviruses have this added complexity for priming plus-strand DNA synthesis, but the mechanism of primer translocation is a potential therapeutic target. As viral replication is necessary for maintenance of the hepadnavirus (including the human pathogen, hepatitis B virus) chronic carrier state, understanding replication and uncovering therapeutic targets is critical for limiting disease in carriers.

In some embodiments, systems and methods of the invention target the HBV genome by finding a nucleotide string within a feature such as PreS1. Guide RNA against PreS1 locates at the 5' end of the coding sequence. Thus it is a good candidate for targeting because it represents one of the 5'-most targets in the coding sequence. Endonuclease digestion will introduce insertion/deletion, which leads to frame shift of PreS1 translation. HBV replicates its genome through the form of long RNA, with identical repeats DR1 and DR2 at both ends, and RNA encapsidation signal epsilon at the 5' end. The reverse transcriptase domain (RT) of the polymerase gene converts the RNA into DNA. Hbx protein is a key regulator of viral replication, as well as host cell functions. Digestion guided by RNA against RT will introduce insertion/deletion, which leads to frame shift of RT translation. Guide RNAs sgHbx and sgCore can not only lead to frame shift in the coding of Hbx and HBV core protein, but also deletion the whole region containing DR2-DR1-Epsilon. The four sgRNA in combination can also lead to systemic destruction of HBV genome into small pieces. In some embodiments, method of the invention include creating one or several guide RNAs against key features within a genome such as the HBV genome shown in FIG. 10.

Figure 11:
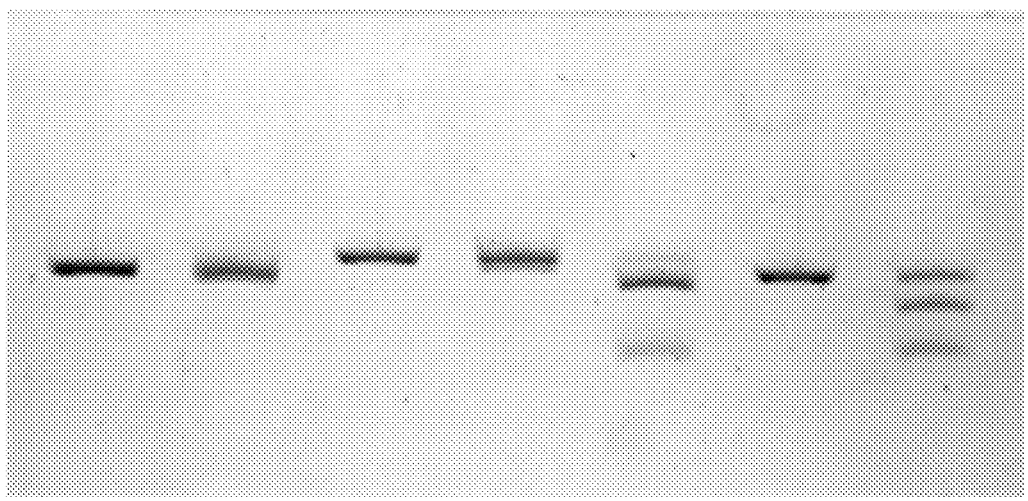
FIG. 11 shows the results of delivering a viral treatment.

FIG. 10 shows key parts in the HBV genome targeted by CRISPR guide RNAs. To achieve the CRISPR activity in cells, expression plasmids coding cas9 and guide RNAs are delivered to cells of interest (e.g., cells carrying HBV DNA). To demonstrate in an in vitro assay, anti-HBV effect may be evaluated by monitoring cell proliferation, growth, and morphology as well as analyzing DNA integrity and HBV DNA load in the cells. The described method may be validated using an in vitro assay. To demonstrate, an in vitro assay is performed with cas9 protein and DNA amplicons flanking the target regions. Here, the target is amplified and the amplicons are incubated with cas9 and a gRNA having the selected nucleotide sequence for targeting. As shown in FIG. 11, DNA electrophoresis shows strong digestion at the target sites.

FIG. 11 shows a gel resulting from an in vitro CRISPR assay against HBV. Lanes 1, 3, and 6: PCR amplicons of HBV genome flanking RT, Hbx-Core, and PreS1. Lane 2, 4, 5, and 7: PCR amplicons treated with sgHBV-RT, sgHBV-Hbx, sgHBV-Core, sgHBV-PreS1. The presence of multiple fragments especially visible in lanes 5 and 7 show that sgHBV-Core and sgHBV-PreS1 provide especially attractive targets in the context of HBV and that use of systems and methods of the invention may be shown to be effective by an in vitro validation assay.

Example 3: Varicella-Zoster Therapy

Shingles—sometimes known as herpes zoster, zoster, chickenpox virus, human herpesvirus type 3 (HHV-3), or zona—is a viral disease characterized by blisters and rash that come with great pain to the patient, which pain lasts as much as four to six weeks. The rash often appears in a characteristic stripe on a side of the body. Some people develop ongoing nerve pain which may last for months or years, a condition called postherpetic neuralgia.

Shingles and postherpetic neuraligia are associated with a reactivation of varicella zoster virus (VZV) within a person. VZV only effects humans and is the cause of chickenpox in young people. VZV infects the nerves, and causes a wide variety of symptoms. After the primary infection (chickenpox), the virus goes dormant in the nerves, including the cranial nerve ganglia, dorsal root ganglia, and autonomic ganglia. Many years after the patient has recovered from chickenpox, VZV can reactivate to cause a number of neurologic conditions.

Compositions that include a vector comprising a gene for a nuclease, a sequence that targets the nuclease to a genome of a virus, and a promoter that promotes transcription from the vector within cells of a specific type may be used to treat or prevent conditions such as shingles or postherpetic neuraligia. Using methods and compositions of the invention to treat an infection such as by varicella zoster virus may include delivering the nuclease to specific cell types such as neurons.

Methods of the invention include targeting vectors to neurons and other cell types. Any suitable targeting method can be used. For example, targeting can include microsurgery or using the cytomegalovirus (CMV) promoter (11) or the Rous sarcoma virus (RSV) enhancerypromoter (pRcRSV, Invitrogen) as described in Glatzel et al., 2000, Adenoviral and adeno-associated viral transfer of genes to the peripheral nervous system PNAS 97(1):442-447, incorporated by reference. For the promoters, see also Liu et al., 2004, CMV enhancer/human PDGF-beta promoter for neuron specific transgene expression, Gene Ther 11(1):52-60, incorporated by reference. For additional discussion of targeting neurons, see Sapunar et al., 2012, Dorsal root ganglion—a potential new therapeutic target for neuropathic pain, J Pain Res 5:31-38, incorporated by reference. Delivering an active targetable nuclease specifically to neurons (and preferably the DRG) may be used to treat or prevent shingles or postherpetic neuralgia. In the nerve cells, the promoter causes the expression of the genes selectively within the nerve cells. The promoter may be, for example, a cytomegalovirus promoter, a Rous sarcoma virus promoter, or a platelet-derived growth factor (PGDF) promoter.

The tageting sequence may be designed to target a regulatory element in the genome of the virus and preferably lacks any exact match in a human genome. The targeting sequence may be a portion of the vector that codes for a gRNA. The nuclease may be a cas9 endonuclease. In some embodiments, the sequence is within a clustered regularly interspaced short palindromic repeats (CRISPR) region within the vector, and the CRISPR region encodes a plurality of guide RNAs that match a plurality of targets within the genome of the virus.

What is claimed is:

1. A composition for treating an Epstein-Barr virus (EBV) viral infection, the composition comprising:
a CRISPR/Cas9 plasmid comprising (a) a nucleic acid molecule under the control of a regulatory sequence and encoding a guide RNA that hybridizes to a complementary sequence in a target EBV genome, wherein the complementary sequence in the target EBV genome comprises a sequence selected from the group consisting of SEQ ID NO: 1, SEQ ID NO: 2, SEQ ID NO: 3, SEQ ID NO: 4, SEQ ID NO: 5, SEQ ID NO: 6, and SEQ ID NO: 7; (b) a nucleic acid molecule under the control of a regulatory sequence and encoding a gene for a Cas9 endonuclease; and (c) an EBV origin of replication;
wherein delivery of the plasmid to EBV-infected eukaryotic cells causes the EBV-infected eukaryotic cells to express the guide RNA and the Cas9 endonuclease leading to reduced EBV load relative to untreated EBV-infected eukaryotic cells.

2. The composition of claim 1, wherein the plasmid encodes a plurality of guide RNAs.

3. The composition of claim 1, wherein the complementary sequence in the target EBV genome comprises SEQ ID NO: 2.

4. The composition of claim 1, wherein the complementary sequence in the target EBV genome comprises SEQ ID NO: 6.

5. The composition of claim 1, wherein the complementary sequence in the target EBV genome comprises SEQ ID NO: 1 and further wherein the plasmid encodes: a second guide RNA that hybridizes to a second complementary sequence in the target EBV genome comprising SEQ ID NO: 2; and a third guide RNA that hybridizes to a third complementary sequence in the target EBV genome comprising SEQ ID NO: 6.

6. The composition of claim 1, wherein the complementary sequence in the target EBV genome comprises SEQ ID NO: 4 and further wherein the plasmid encodes a second guide RNA that hybridizes to a second complementary sequence in the target EBV genome comprising SEQ ID NO: 5.

7. The composition of claim 1, wherein the complementary sequence in the target EBV genome comprises SEQ ID NO: 3.

8. The composition of claim 1, wherein the complementary sequence in the target EBV genome comprises SEQ ID NO: 4 and further wherein the plasmid encodes: a second guide RNA that hybridizes to a second complementary sequence in the target EBV genome comprising SEQ ID NO: 5; and a third guide RNA that hybridizes to a third complementary sequence in the target EBV genome comprising SEQ ID NO: 3.

9. The composition of claim 1, wherein the complementary sequence in the target EBV genome comprises SEQ ID NO: 1 and further wherein the plasmid encodes:

a second guide RNA that hybridizes to a second complementary sequence in the target EBV genome comprising SEQ ID NO: 2;

a third guide RNA that hybridizes to a third complementary sequence in the target EBV genome comprising SEQ ID NO: 3;

a fourth guide RNA that hybridizes to a fourth complementary sequence in the target EBV genome comprising SEQ ID NO: 4;

a fifth guide RNA that hybridizes to a fifth complementary sequence in the target EBV genome comprising SEQ ID NO: 5;

a sixth guide RNA that hybridizes to a sixth complementary sequence in the target EBV genome comprising SEQ ID NO: 6; and a seventh guide RNA that hybridizes to a seventh complementary sequence in the target EBV genome comprising SEQ ID NO: 7.

10. The composition of claim 1, wherein the complementary sequence in the target EBV genome comprises SEQ ID NO: 3 and further wherein the plasmid encodes a second guide RNA that hybridizes to a second complementary sequence in the target EBV genome comprising SEQ ID NO: 7.

11. The composition of claim 1, wherein the complementary sequence in the target EBV genome comprises SEQ ID NO: 1.

12. The composition of claim 1, wherein the complementary sequence in the target EBV genome comprises SEQ ID NO: 5.

13. The composition of claim 1, wherein the complementary sequence in the target EBV genome comprises SEQ ID NO: 7.

14. The composition of claim 1, wherein the complementary sequence in the target EBV genome comprises SEQ ID NO: 4.

* * * * *